United States Patent
Alter et al.

(10) Patent No.: US 11,498,958 B2
(45) Date of Patent: Nov. 15, 2022

(54) METHODS OF DIAGNOSIS AND TREATMENT OF TUBERCULOSIS AND INFECTION

(71) Applicants: THE GENERAL HOSPITAL CORPORATION, Boston, MA (US); PRESIDENT AND FELLOWS OF HARVARD COLLEGE, Cambridge, MA (US)

(72) Inventors: Galit Alter, Winchester, MA (US); Sarah Fortune, Cambridge, MA (US); Amy Chung, Melbourne (AU)

(73) Assignees: THE GENERAL HOSPITAL CORPORATION, Boston, MA (US); PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 0 days.

(21) Appl. No.: 16/998,036

(22) Filed: Aug. 20, 2020

(65) Prior Publication Data
US 2021/0147520 A1    May 20, 2021

Related U.S. Application Data

(63) Continuation of application No. 15/520,432, filed as application No. PCT/US2015/056574 on Oct. 21, 2015, now abandoned.

(60) Provisional application No. 62/066,494, filed on Oct. 21, 2014.

(51) Int. Cl.
| | |
|---|---|
| *C07K 16/12* | (2006.01) |
| *A61K 38/00* | (2006.01) |
| *A61K 39/395* | (2006.01) |
| *C07K 7/08* | (2006.01) |
| *C07K 14/35* | (2006.01) |
| *A61K 39/00* | (2006.01) |
| *C07K 16/00* | (2006.01) |

(52) U.S. Cl.
CPC .......... *C07K 16/1289* (2013.01); *A61K 38/00* (2013.01); *A61K 39/395* (2013.01); *C07K 7/08* (2013.01); *C07K 14/35* (2013.01); *A61K 39/00* (2013.01); *C07K 16/00* (2013.01); *C07K 2317/41* (2013.01); *C07K 2317/70* (2013.01); *C07K 2317/732* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 7,687,060 B2 | 3/2010 | Jolles et al. | |
| 8,183,000 B2 | 5/2012 | Block et al. | |
| 2002/0098200 A1 * | 7/2002 | Campos-Neto | A61P 37/04 424/190.1 |
| 2006/0252075 A1 | 11/2006 | Zagury et al. | |
| 2008/0311159 A1 | 12/2008 | Klein et al. | |
| 2011/0014335 A1 | 1/2011 | Dyess | |
| 2011/0021367 A1 | 1/2011 | Gopal | |
| 2013/0149300 A1 | 6/2013 | Hiatt et al. | |
| 2013/0280238 A1 | 10/2013 | Evans et al. | |

FOREIGN PATENT DOCUMENTS

| | | |
|---|---|---|
| AU | 2010224461 B2 | 10/2010 |
| WO | 2012164088 A1 | 6/2012 |
| WO | WO-2012164088 A1 * | 12/2012 ......... G01N 33/5695 |

OTHER PUBLICATIONS

Ackerman et al., "Natural variation in Fc glycosylation of HIV-specific antibodies impacts antiviral activity", J Clin Invest. 123(5):12183-2192 (2013).
Anthony et al., "Intravenous gammaglobulin suppresses inflammation through a novel T H 2 pathway." Nature 475 (7354):1110-113 (2011).
Anthony et al., "Recapitulation of IVIG anti-inflammatory activity with a recombinant IgG Fc." Science 320(5874):1373-376 (2008).
Anthony et al., "The N Domain of Human Angiotensin-I-converting Enzyme The Role of N-Glycosylation and the Crystal Structure in Complex with an N Domain-Specific Phosphinic Inhibitor, RXP407." J. Biol Chem 285(46):35685-35693 (2010).
Brust et al., "*Mycobacterium tuberculosis* lipolytic enzymes as potential biomarkers for the diagnosis of active tuberculosis." PloS One 6(9):e25078 (2011).
Calarese et al., "Antibody domain exchange is an immunological solution to carbohydrate cluster recognition." Science 300(5628):2065-2071 (2003).
Caragea et al., "Glycosylation site prediction using ensembles of Support Vector Machine classifiers", BMC Bioinformatics 8:438 (2007).
Fotinopoulou et al., "Screening for glycosylation changes on recombinant human IgG using lectin methods." Biotechnology and Applied Biochemistry 37(1):1-7 (2003).
Go et al., "Glycosylation site-specific analysis of clade C HIV-1 envelope proteins", J Proteome Res 8(9):4231-4242 (2009).
Gornik et al., "Fucosylation of IgG heavy chains is increased in rheumatoid arthritis." Clinical Biochemistry 32 (8):605-608 (1999).

(Continued)

*Primary Examiner* — Oluwatosin A Ogunbiyi
(74) *Attorney, Agent, or Firm* — Nixon Peabody LLP; David S. Resnick; Nicole D. Kling

(57) ABSTRACT

Described herein are methods of treating, diagnosing, and/or prognosing a disease in a subject relating to detection of the glycosylation state of the antibodies present in the subject. In some embodiments, the disease can be an infection. In some embodiments, an antibody glycosylation state that is indicative of the presence of a disease, or a need for treatment of a disease can be reduced glycosylation (e.g., galactosylation, sialation, fucosylation, and/or afucosylated branched glycoforms).

3 Claims, 18 Drawing Sheets

(56) References Cited

OTHER PUBLICATIONS

Jefferis et al., "Glycosylation of antibody molecules: structural and functional significance." Antibody Engineering 65:111-128 (1997).
Julien et al., "Crystal structure of a soluble cleaved HIV-1 envelope trimer." Science 342:1477-1783 (2013).
Kolchinsky et al., "Increased neutralization sensitivity of CD4-independent human immunodeficiency virus ariants." Journal of Virology 75(5):2041-2050 (2001).
Kong et al., "Supersite of immune vulnerability on the glycosylated face of HIV-1 envelope glycoprotein gp120." Mature Structural and Molecular Biology 20(7):796-803 (2013).
Kwong et al., "Structure of an HIV gp120 envelope glycoprotein in complex with the CD4 receptor and a neutralizing human antibody." Nature 393(6686):648-659 (1998).
Lyumkis et al., "Cryo-EM structure of a fully glycosylated soluble cleaved HIV-1 envelope trimer." Science 342(6165):1484-1490 (2013).
McGuire et al., "Engineering HIV envelope protein to activate germline B cell receptors of broadly neutralizing anti-CD4 binding site antibodies." Journal of Experimental Medicine 210:655-663 (2013).
McLellan et al., "Structure of HIV-1 gp120 V1/V2 domain with broadly neutralizing antibody PG9." Nature 480 (7377):336-343 (2011).
Mehta et al., "Increased levels of galactose-deficient anti-Gal immunoglobulin G in the sera of hepatitis C virus-infected individuals with fibrosis and cirrhosis", Journal of Virology 82(3):1259-1270 (2008).
Pancera et al., "Structural basis for diverse N-glycan recognition by HIV-1-neutralizing V1-V2-directed antibody PG16." Nature Structural and Molecular Biology 20(7):804-813 (2013).
Pejchal et al., "A potent and broad neutralizing antibody recognizes and penetrates the HIV glycan shield." Science 334(6059):1097-1103 (2011).
Poon et al., "Evolutionary interactions between N-linked glycosylation sites in the HIV-1 envelope", PLoS Comput Biol 3(1) e11 (2007).
Rademacher et al., "The role of IgG glycoforms in the pathogenesis of rheumatoid arthritis." Springer Seminars in Immunopathology 10(2-3):231-249 (1988).
Scallon et al., "Higher levels of sialylated Fc glycans in immunoglobulin G molecules can adversely impact functionality." Molecular Immunology 44(7):1524-1534 (2007).
Selman et al., "Changes in Antigen-specific IgG1 Fc N-glycosylation Upon Influenza and Tetanus Vaccination", Mol. Cell Proteomics 11(4):1-10 (2012).
Shade et al., "Antibody glycosylation and inflammation." Antibodies 2(3):392-414 (2013).
SPARTAC Trial Investigators. "Short-course antiretroviral therapy in primary HIV infection." N Engl J Med 2013 (368):207-217 (2013).
Stadlmann et al., "Analytical and functional aspects of antibody sialylation." J Clin Immunol 30(1):15-19 (2010).
Williams et al., "HIV-1 DNA predicts disease progression and post-treatment virological control." Elife 3 e03821:1-16 (2014).
Wyatt et al., "Functional and immunologic characterization of human immunodeficiency virus type 1 envelope glycoproteins containing deletions of the major variable regions." Journal of Virology 67(8):4557-4565 (1993).

* cited by examiner

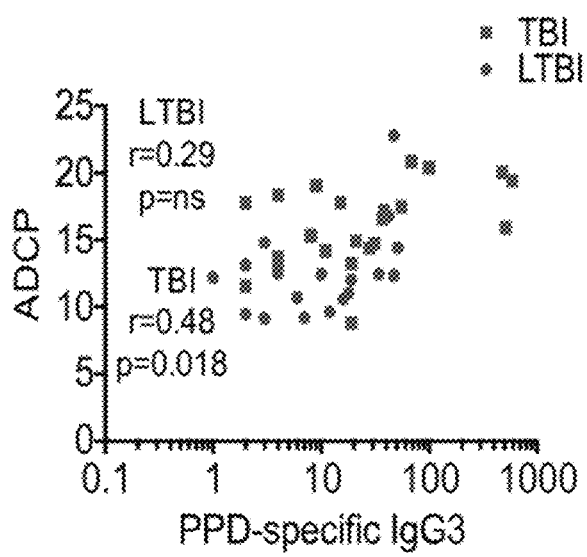
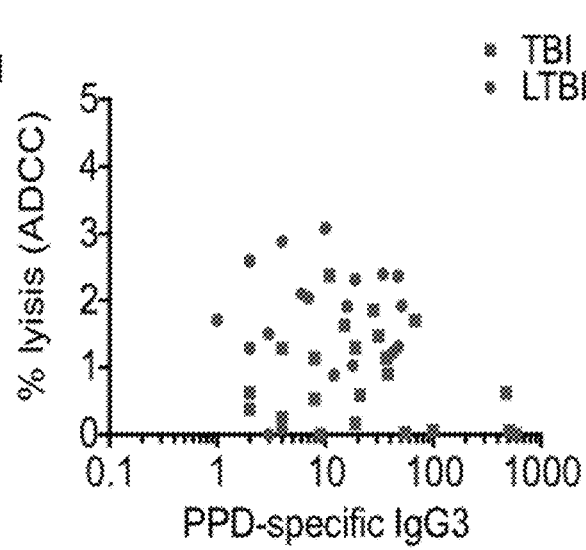
Fig. 5A
Fig. 5B
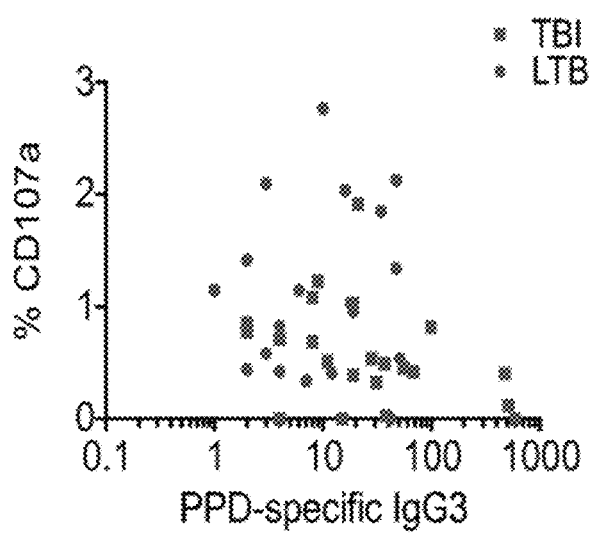
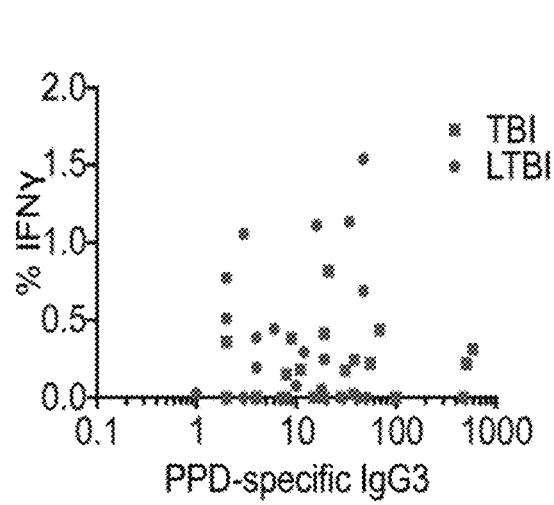
Fig. 5C
Fig. 5D

Total IgG Glyans

PPD-specific IgG Glyans

METHODS OF DIAGNOSIS AND TREATMENT OF TUBERCULOSIS AND INFECTION

CROSS-REFERENCE TO RELATED APPLICATIONS

This application is continuation under 35 U.S.C. § 120 of application U.S. Ser. No. 15/520,432 filed Apr. 20, 2017 now abandoned, which is a 35 U.S.C. § 371 National Phase Entry Application of International Application No. PCT/US2015/056574 filed Oct. 21, 2015, which designates the U.S. and claims benefit under 35 U.S.C. § 119(e) of U.S. Provisional Application No. 62/066,494 filed Oct. 21, 2014, the contents of which are incorporated herein by reference in their entireties.

GOVERNMENT SUPPORT

This invention was made with government support under AI007387 and AI060354 awarded by the National Institutes of Health. The government has certain rights in this invention.

TECHNICAL FIELD

The technology described herein relates to the diagnosis, prognosis, and/or treatment of diseases, e.g., infections.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Tuberculosis (TB) has and continues to be one of the world's deadliest diseases, with over 9 million new cases of infection by the disease causing bacterium, *Mycobacterium tuberculosis* (Mtb), and causing an estimated 1.7 million fatalities every year. Despite centuries of research, the struggle to eradicate tuberculosis continues. Although there is a licensed TB vaccine currently in use, Bacille Calmette-Guérin (BCG) vaccination, this vaccine has variable efficacy, with trials reporting a diverse range of protection and an average efficacy of approximately 50%. Furthermore, it is established that this vaccine primarily protects children from TB meningitis, but is ineffective in preventing pulmonary tuberculosis. Thus new efficacious vaccine strategy approaches, an improved ability to diagnose the disease and novel antibiotics are urgently needed.

Approximately 90% of adults infected with Mtb never develop symptoms of clinical disease, resulting in latent TB infections (LTBI). Although the immune correlates of TB control and protection are not known, individuals with defective cell-mediated immunity have a predisposition towards developing more severe disease. Yet, to date, the importance of host humoral immunity in controlling tuberculosis is particularly unclear.

SUMMARY

As described herein, the inventors have discovered that in a diseased subject, e.g. a subject with an infection, the glycosylation status of the antibodies present in the subject will vary from the glycosylation status of the antibodies present in a healthy individual. In some embodiments, this change in glycosylation status is not limited to antibodies that recognize an antigen associated with the infection. Accordingly, provided herein are methods of diagnosis, prognosis, and treatment that relate to detecting the glycosylation status of one or more antibodies in the subject.

In one aspect, described herein is a method of treating a disease or condition in a subject, the method comprising: assaying a sample obtained from the subject determine the presence or absence of an antibody glycosylation state indicative of the disease or condition; and administering a treatment for the disease or condition if the antibody glycosylation state is indicative of the presence of the disease or condition.

In one aspect, described herein is a method of diagnosing a disease in a subject, comprising: assaying a sample obtained from the subject to determine the presence or absence of an antibody glycosylation state indicative of the disease; diagnosing the disease in the subject based upon the presence of an antibody glycosylation state indicative of the disease. In one aspect, described herein is a method of diagnosing susceptibility for a disease in a subject, comprising: assaying a sample obtained from the subject to determine the presence or absence of an antibody glycosylation state indicative of susceptibility for the disease; and diagnosing susceptibility for the disease in the subject based upon the presence of an antibody glycosylation state indicative of the disease.

In one aspect, described herein is a method of prognosing a disease of condition in a subject, comprising: assaying a sample obtained from the subject to determine the presence or absence of an antibody glycosylation state which varies by a statistically significant amount relative to levels found in a healthy individual; and prognosing an aggressive form of the disease or condition based on the presence of an antibody glycosylation state which varies by a statistically significant amount relative to levels found in a healthy individual.

In one aspect, described herein is a method of detecting infection in a subject, comprising: isolating pathogen specific IgG antibody from a biological sample and/or tissue obtained from the subject; profiling variable glycan decoration on the Fc region of the pathogen specific antibody; and detecting an active infection based on the presence of an altered glycan display on the Fc region of the pathogen specific antibody relative to an individual with latent pathogenic infection. In some embodiments of any of the aspects described herein, the subject does not have signs and/or symptoms of said pathogenic infection. In some embodiments of any of the aspects described herein, infection is detected at point-of-care.

In some embodiments of any of the aspects described herein, the disease is an infection. In some embodiments of any of the aspects described herein, the disease is elderly flu, syphilis, legionella, lyme disease and/or CMV reactivation.

In some embodiments of any of the aspects described herein, the antibody glycosylation state indicative of the disease comprises less glycosylation relative to levels found in a normal individual. In some embodiments of any of the aspects described herein, the antibody glycosylation state comprises less galactosylation, sialation, and/or fucosylation relative to levels found in a normal individual. In some embodiments of any of the aspects described herein, the antibody glycosylation state is marked by one or more different glycan structures relative to a normal individual attached to an antibody Fc-domains. In some embodiments of any of the aspects described herein, the antibody glycosylation state is marked by one or more different glycan structures relative to a latent infected patient attached to an antibody Fc-domain. In some embodiments of any of the aspects described herein, the antibody glycosylation state indicative of the disease is a decreased presence of afucosylated branched glycoforms on bulk IgG.

In some embodiments of any of the aspects described herein, the antibody glycosylation state indicative of the disease comprises an inflamed antibody Fc-domain. In some embodiments of any of the aspects described herein, the antibody is an IgG antibody. In some embodiments of any of the aspects described herein, the antibody is an IgG antibody from the plasma of the subject. In some embodiments of any of the aspects described herein, the antibody is antigen specific to the disease. In some embodiments of any of the aspects described herein, the treatment comprises a therapeutically effective dosage of antibody with a normal level of glycosylation relative to a healthy individual.

In some embodiments of any of the aspects described herein, the disease is tuberculosis (TB). In some embodiments of any of the aspects described herein, the tuberculosis is active TB. In some embodiments of any of the aspects described herein, the glycosylation state indicative of tuberculosis is selected from the group consisting of: decreased 2-galactose (G2): decreased fucosylated G2 (G2F); decreased fucosylated G2 with bisecting N-acetylglucosamine (G2FB); and decreased 2-galactose (G2), fucosylated G2 (G2F), and fucosylated G2 with bisecting N-acetylglucosamine (G2FB).

In some embodiments of any of the aspects described herein, the condition is transplant rejection. In some embodiments of any of the aspects described herein, the glycosylation state indicative of transplant rejection is selected from the group consisting of: increased G0FB; increased G0F; and increased G0F and G0FB but not increased G0B.

In some embodiments of any of the aspects described herein, the condition is flu non-responsiveness. In some embodiments of any of the aspects described herein, the glycosylation state indicative of flu non-responsiveness is selected from the group consisting of increased G1; increased G0B; decreased G0F; and increased G1 and G0B but not increased G0F. In some embodiments of any of the aspects described herein, the treatment of flu non-responsiveness comprises decreasing the level and/or activity of G1 and/or G0B antibodies in the subject.

BRIEF DESCRIPTION OF THE FIGURES

Exemplary embodiments are illustrated in referenced figures. It is intended that the embodiments and figures disclosed herein are to be considered illustrative rather than restrictive.

FIG. 1B depicts a comparison of PPD-specific binding at 100 ug/ml by luminex assay.

(FIG. 2B) ADCC activity by RFADCC using isolated NK cells, antibody mediated activation of NK cells as measured by (FIG. 2C) CD107a degranulation and (FIG. 2D) IFNγ secretion, all assays were tested at 100 ug/ml concentration of purified subject IgG. As the PPD-specific titer can influence strength of Fc-mediated function, Fc-activity was normalized to their respective PPD-specific Ab titers measured at 100 ug/ml, to more accurately compare the Fc-activity of the respective TB cohorts. Data normalized by titer are plotted for (FIG. 2E) ADCP; (FIG. 2F) ADCC; Fc-mediated NK cell activation as determined by (FIG. 2G) CD107a degranulation and (FIG. 2H) IFN-γ expression.

(FIG. 3G) ADCC; Fc-mediated NK cell activation as determined by (FIG. 3H) CD107a degranulation and (FIG. 3I) IFN-γ expression was correlated with FcRIIIa binding. Circles identify LTBI subjects, squares TBI subjects.

FIGS. 5A-5G demonstrate that IgG3 subclass mediates PPD-specific ADCP activity. IgG3 was the only subclass significantly different between the LTBI and TBI subjects, thus to determine if IgG3 subclass influenced antibody-dependent cellular function, IgG3 was correlated with Fc-functions (FIG. 5A) ADCP, (FIG. 5B) ADCC, Fc-mediated NK cell activation as determined by (FIG. 5C) CD107a degranulation and (FIG. 5D) IFN-γ expression, as well as the previously mentioned FcRs: (FIG. 5E) FcRIIa, (FIG. 5F) FcRIIb, (FIG. 5G) FcRIIIa.

(FIGS. 6A and 6G) % Total G0 (Galactose-0), then G0 glycoforms further resolved as (FIGS. 6B and 6H) % Total G0F (fucose) and (FIGS. 6C and 6I) % Total G0B (Bisecting N-GlcNAc) glycans. G2 glycoforms differences were also observed (FIGS. 6D and 6J) G2, (FIGS. 6E and 6K) G2F and (FIGS. 6F and 6L) G2B structures were compared.

DETAILED DESCRIPTION

All references cited herein are incorporated by reference in their entirety as though fully set forth. Unless defined otherwise, technical and scientific terms used herein have the same meaning as commonly understood by one of ordinary skill in the art to which this invention belongs. Singleton et al., Dictionary of Microbiology and Molecular Biology 4th ed., J. Wiley & Sons (New York, N.Y. 2012); March, Advanced Organic Chemistry Reactions, Mechanisms and Structure 5th ed., J. Wiley & Sons (New York, N.Y. 2001); and Sambrook and Russel, Molecular Cloning: A Laboratory Manual 4th ed., Cold Spring Harbor Laboratory Press (Cold Spring Harbor, N.Y. 2012); provide one skilled in the art with a general guide to many of the terms used in the present application.

As disclosed herein, tuberculosis (TB) continues to be a principal infectious disease. To date, the importance of host humoral immunity in controlling tuberculosis is particularly unclear. The inventors found that TB-specific IgG purified from patient plasma are capable of recruiting innate immune effector cells to mediate Fc-effector responses. In addition, Abs from patients with active TB infection were found to be distinct both in biophysical character and function from those in patients with latent TB infection. In particular, IgG from TB subjects were able to mediate stronger antibody dependent cellular cytotoxicity (ADCC). Modulation of the different Fc-mediate effector responses was correlated with the highly functional IgG-3 subclass and coincided with alterations of Fc glycosylation structures, specifically decreased presence of afucosylated branched glycoforms on bulk IgG. In accordance with various embodiments herein, analysis of Fc-glycosylation structures of plasma IgG may be used as a diagnostic tool to predict outcome of TB infection. In accordance with various embodiments herein, TB vaccination strategies may include consideration of the role of glycosylated IgG3 subclass as an inducer of Fc-effector function to help control mTB.

In some embodiments, glycosylation on any of the 4 IgG subclasses (i.e. IgG1, IgG2, IgG3, and IgG4) and/or on other Ig types (e.g. IgM and IgE) can be determined in the methods described herein, e.g. the glycosylation state of any of these antibodies can be determined as described in the methods of treatment and/or diagnosis described herein. In some embodiments, the glycosylation state of IgG antibodies is determined. In some embodiments, the glycosylation state of IgG3 antibodies is determined.

Figure 8A:
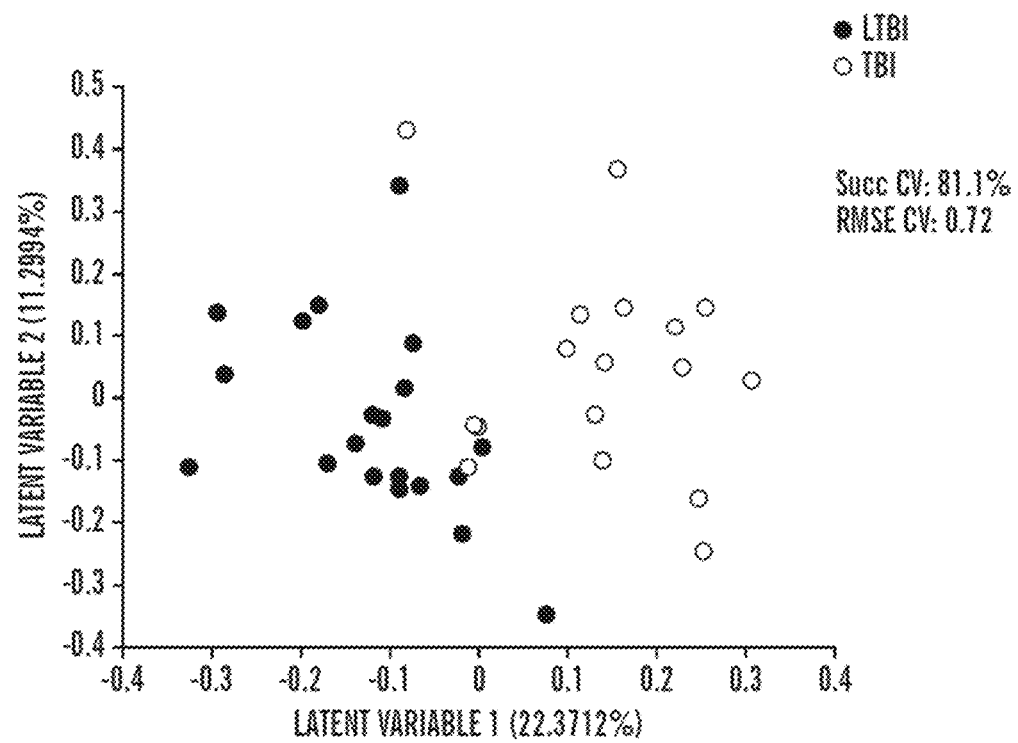
FIGS. 8A-8C demonstrate the resolution of the differences in antibody parameters among LTBI and TBI samples using (FIG. 8A) function and isotype alone, (FIG. 8B) glycan alone, and (FIG. 8C) combined function, isotype and glycan. The latter demonstrates 91% resolving power.
Figure 8A:
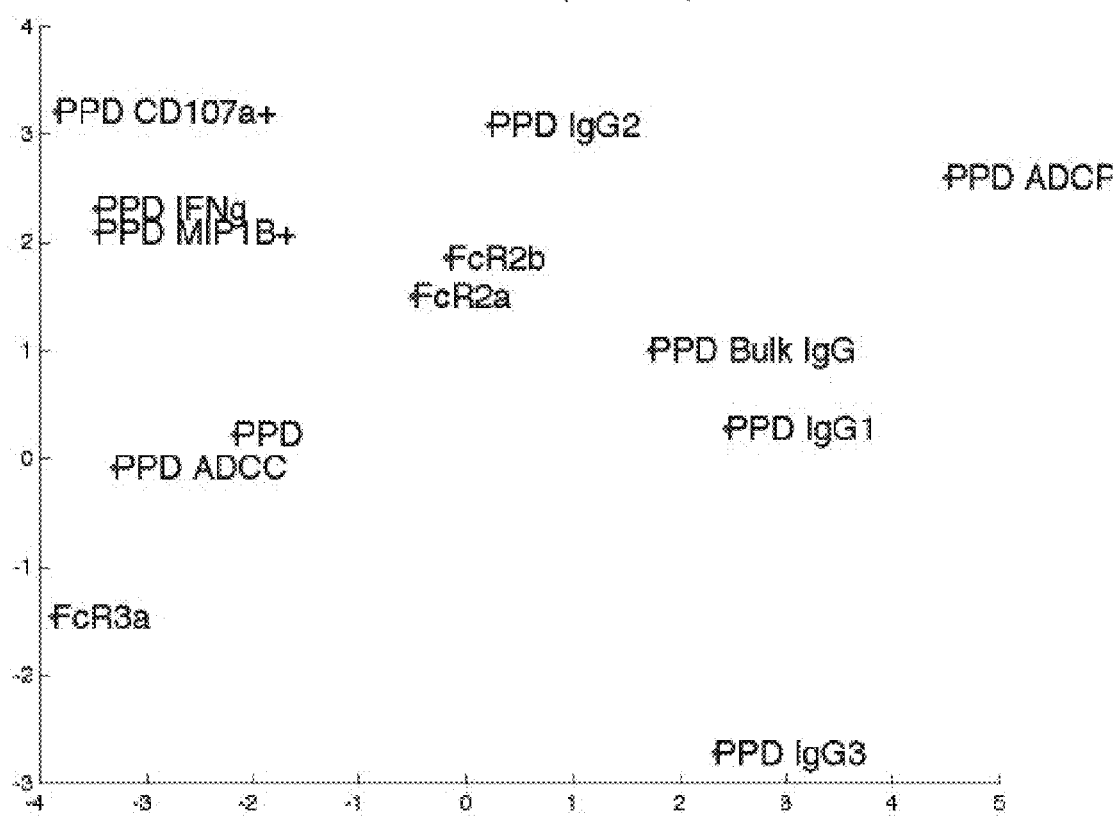
Figure 8B:
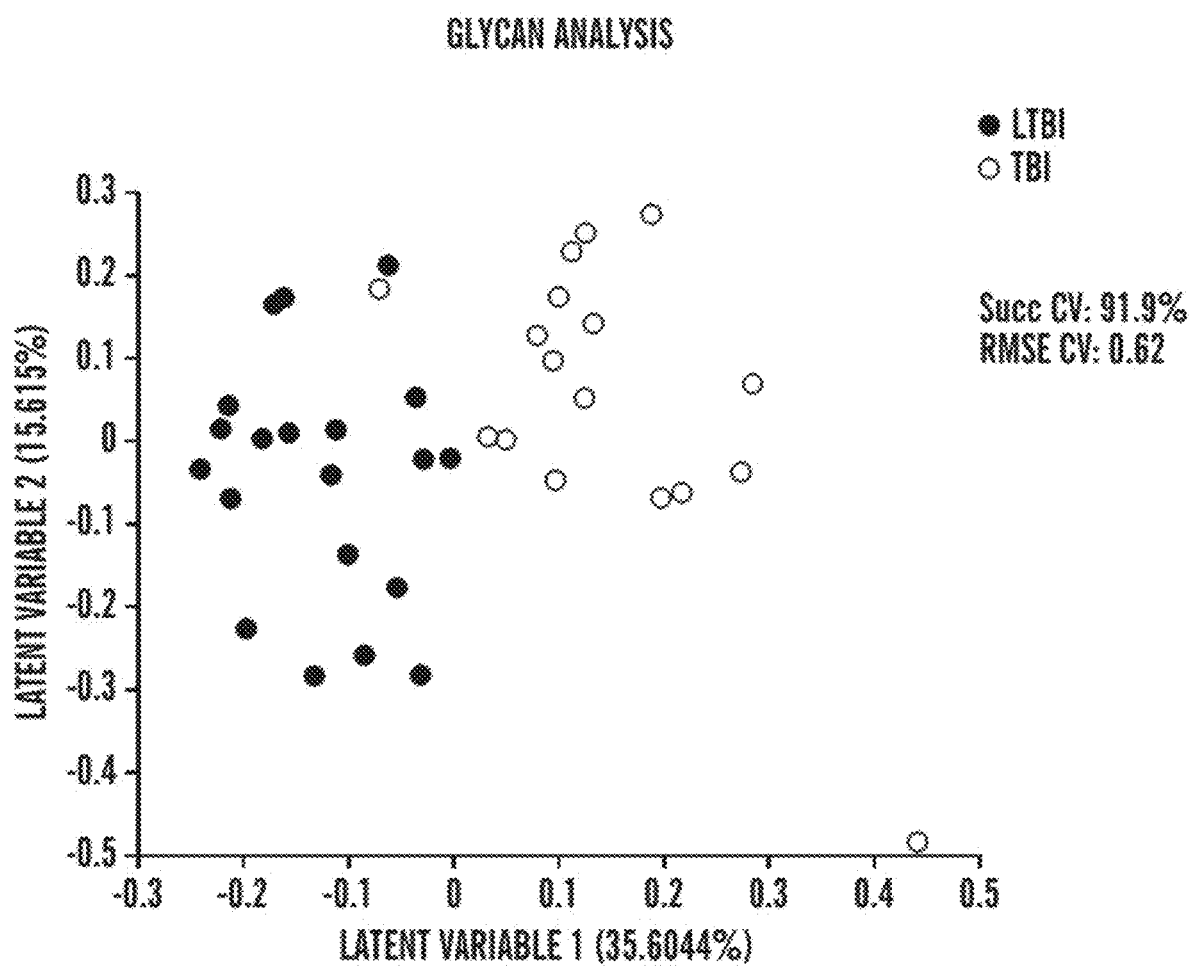
Figure 8B:
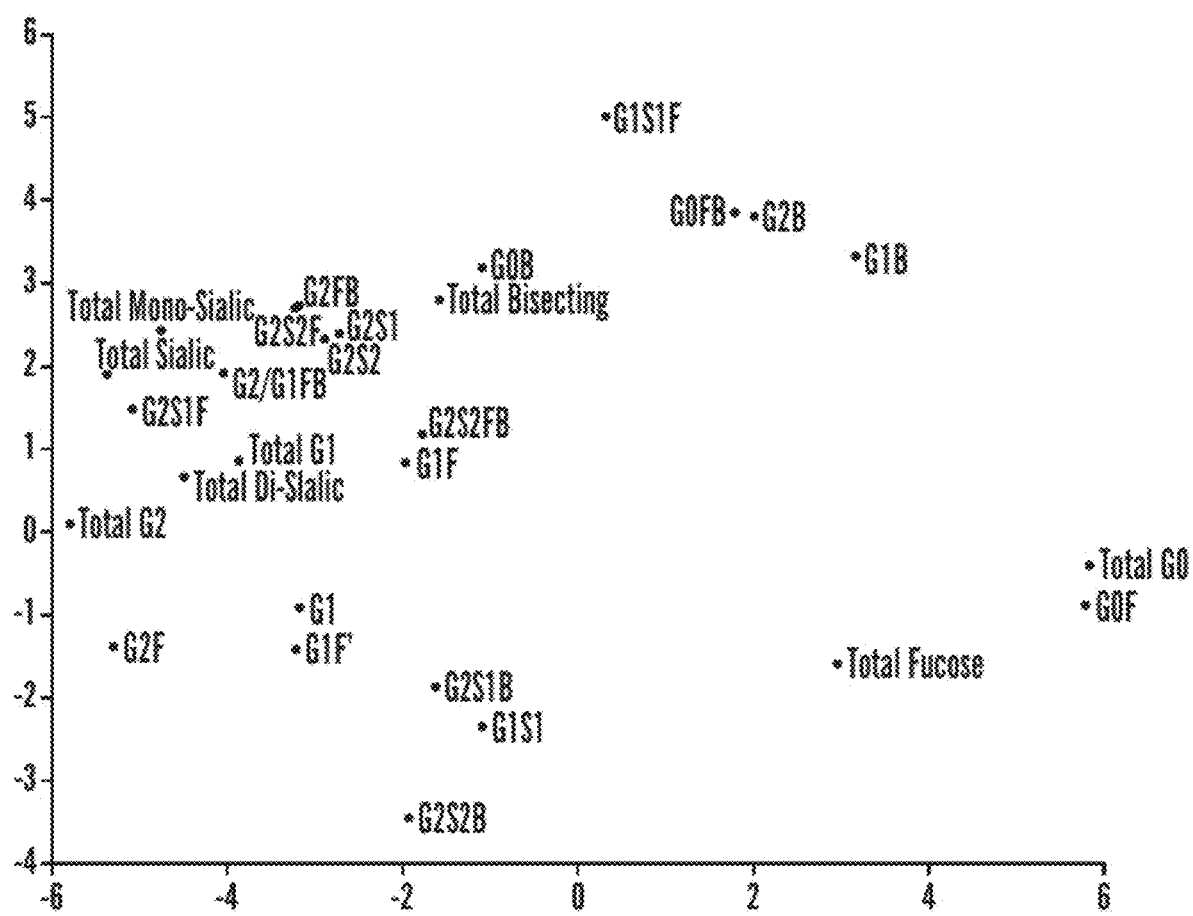
Figure 8C:
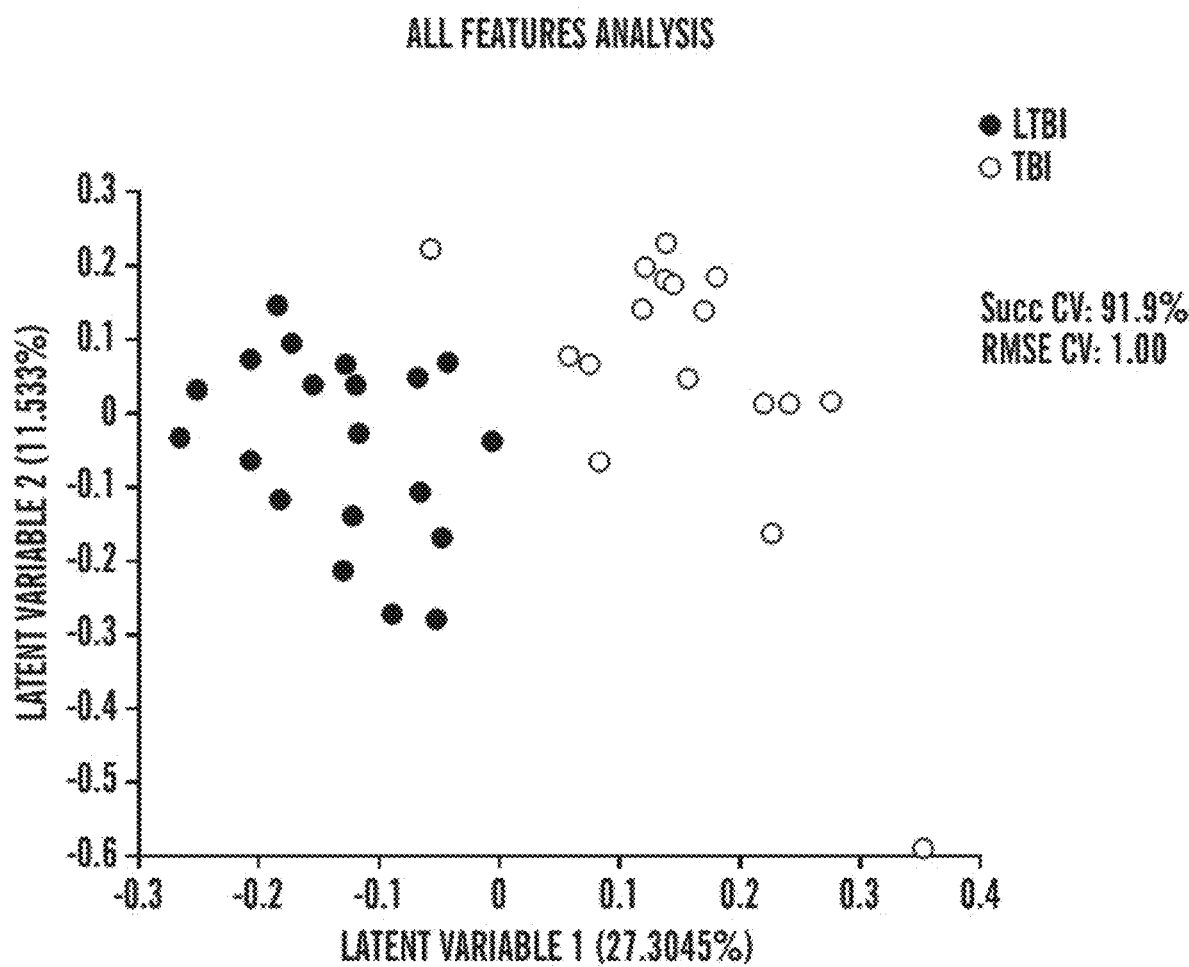
Figure 8C:
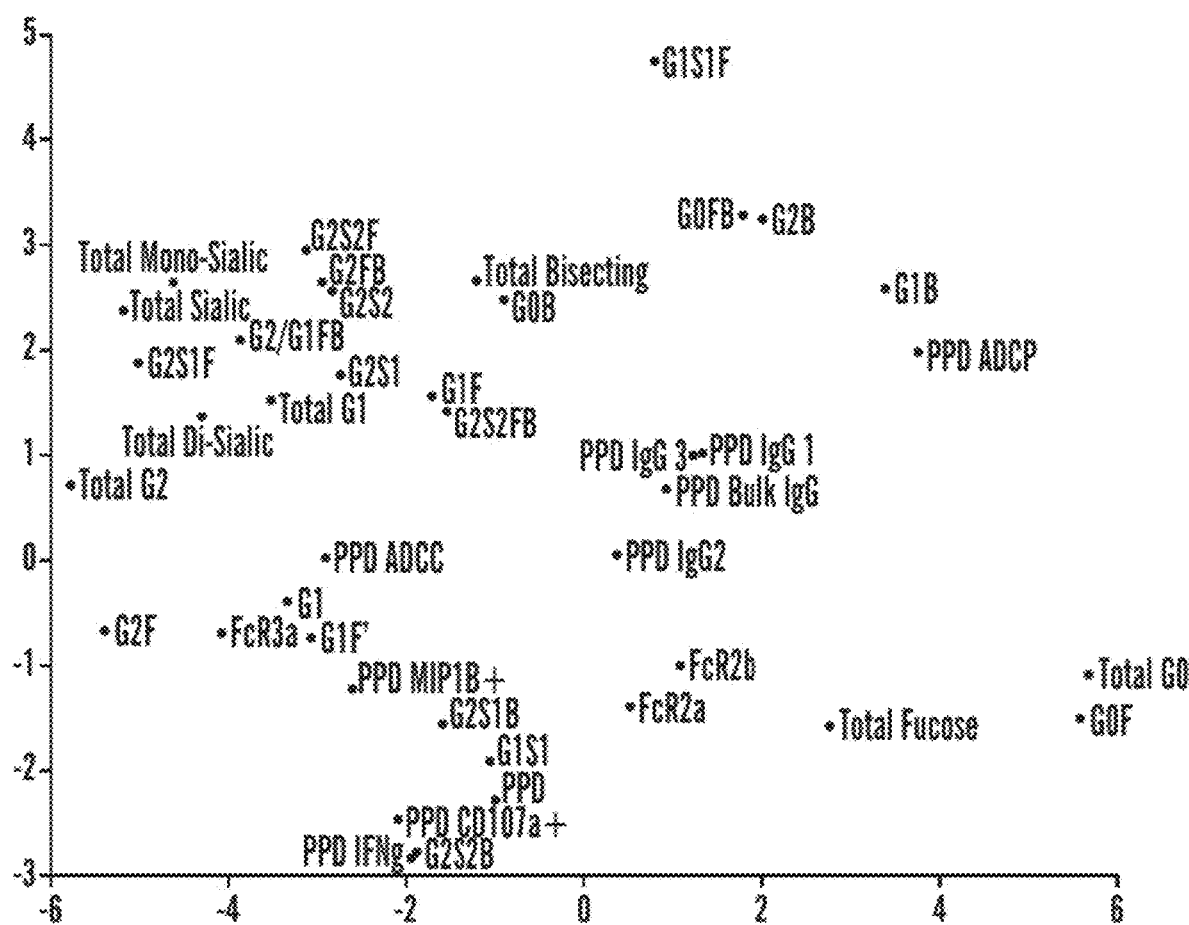

In one embodiment herein, the present invention provides a method of diagnosing a disease in a subject, comprising obtaining a sample from the subject, assaying the sample to determine the presence or absence of an antibody glycosylation state indicative of the disease, and diagnosing the disease in the subject based upon the presence of an antibody glycosylation state indicative of the disease. As described herein, (see, e.g. FIG. 8A-8C), classification and/or stratification of subjects by means of IgG subclass provides incomplete resolution, whereas the use of glycosylation states, as described herein, provides improved results. In another embodiment, the assay is a serological assay adapted to detect the presence of an antibody glycosylation state. In another embodiment, the subject does not display significant clinical symptoms of the disease. In another embodiment, the disease is tuberculosis (TB), an active state of TB, and/or an infection. In another embodiment, the disease is elderly flu, syphilis, legionella, lyme disease and/or CMV reactivation. In another embodiment, the antibody glycosylation state indicative of the disease comprises less glycosylation relative to levels found in a normal individual. In another embodiment, the antibody glycosylation state comprises less galactosylation, sialation, and/or fucosylation relative to levels found in a normal individual. In another embodiment, the antibody glycosylation state is marked by one or more different glycan structures relative to a normal individual attached to an antibody Fc-domains. In another embodiment, the antibody glycosylation state is marked by one or more different glycan structures relative to a latent infected patient attached to an antibody Fc-domain. In another embodiment, the antibody glycosylation state indicative of the disease comprises an inflamed antibody Fc-domain. In another embodiment, the antibody is an IgG antibody. In another embodiment, the antibody is an IgG antibody from the plasma of the subject. In another embodiment, the antibody glycosylation state indicative of the disease is a decreased presence of afucosylated branched glycoforms on bulk IgG. In another embodiment, the antibody is antigen specific to the disease.

In another embodiment, the present invention provides a method of diagnosing susceptibility for a disease in a subject, comprising obtaining a sample from the subject, assaying the sample to determine the presence or absence of an antibody glycosylation state indicative of susceptibility for the disease, and diagnosing susceptibility for the disease in the subject based upon the presence of an antibody glycosylation state indicative of the disease. In another embodiment, the assay is a serological assay adapted to detect the presence of an antibody glycosylation state. In another embodiment, the subject does not display significant clinical symptoms of the disease. In another embodiment, the disease is tuberculosis (TB), an active state of TB, and/or an infection. In another embodiment, the antibody is an IgG antibody from the plasma of the subject. In another embodiment, the antibody glycosylation state indicative of the disease is a decreased presence of afucosylated branched glycoforms on bulk IgG.

In another embodiment, the present invention provides a method of treating a disease, comprising diagnosing the disease in the subject based upon the presence of an antibody glycosylation state indicative of the disease, and treating the disease. In one aspect, described herein is a method of treating a disease or condition in a subject, the method comprising assaying a sample obtained from the subject determine the presence or absence of an antibody glycosylation state indicative of the disease or condition; and administering a treatment for the disease or condition if the antibody glycosylation state is indicative of the presence of the disease or condition.

In another embodiment, the assay is a serological assay adapted to detect the presence of an antibody glycosylation state. In another embodiment, the subject does not display significant clinical symptoms of the disease. In another embodiment, the disease is active tuberculosis (TB). In another embodiment, the disease is an infection. In another embodiment, the antibody glycosylation state indicative of the disease is a decreased presence of afucosylated branched glycoforms on bulk IgG. In another embodiment, treating the disease comprises administering a therapeutically effective dosage of antibody with a normal level of glycosylation relative to a healthy individual.

Various other embodiments include a method of prognosing a disease in a subject, comprising obtaining a sample from the subject, assaying the sample to determine the presence or absence of a low level of antibody glycosylation state relative to levels found in a healthy individual, and prognosing an aggressive form of the disease based on the presence of a low level of glycosylation state relative to levels found in a healthy individual. In another embodiment, the assay is a serological assay adapted to detect the presence of an antibody glycosylation state. In another embodiment, the subject does not display significant clinical symptoms of the disease. In another embodiment, the disease is tuberculosis (TB). In another embodiment, the aggressive form of the disease is an active state of TB. In another embodiment, the disease is an infection. In another embodiment, the disease is elderly flu, syphilis, legionella, lyme disease and/or CMV reactivation. In another embodiment, the low level of antibody glycosylation state includes less galactosylation, sialation, and/or fucosylation relative to levels found in a normal individual. In another embodiment, the low level of antibody glycosylation state comprises an inflamed antibody Fc-domain. In another embodiment, the antibody is an IgG antibody from the plasma of the subject. In another embodiment, the antibody is antigen specific to the disease. In another embodiment, the low level of antibody glycosylation state is a decreased presence of afucosylated branched glycoforms on bulk IgG.

In another embodiment, the present invention provides a method of detecting infection from a sample, comprising obtaining a biological sample and/or tissue from a subject, isolating pathogen specific IgG antibody from the biological sample and/or tissue, profiling variable glycan decoration on the Fc region of the pathogen specific antibody, and detecting an active infection based on the presence of an altered glycan display on the Fc region of the pathogen specific antibody relative to an individual with latent pathogenic infection. In another embodiment, the subject does not have signs and/or symptoms of said pathogenic infection. In another embodiment, infection is detected at point-of-care. In another embodiment, the infection is from *Mycobacterium tuberculosis*. In another embodiment, the altered glycan display comprises decreased afucosylated branched glycoforms. In another embodiment, the altered glycan display comprises decreased 2-Galactose (G2), Fucosylated G2 (G2F), and/or Fucosylated G2 with bisecting N-acetylglucosamine (G2FB). In another embodiment, the active infection is active tuberculosis (TB). In another embodiment, the infection is associated with elderly flu, syphilis, legionella, lyme disease and/or CMV reactivation.

As used herein, the term "antibody glycosylation state" refers to the pattern, e.g. position, type, frequency, and/or number of glycan residues attached to an antibody and/or population of antibodies. Various glycosylation patterns are described herein. Structural details and methods of detecting such glycosylation states are known in the art, see e.g., Demchenko et al. "Handbook of Chemical Glycosylation" Wiley-VCH, 2008; Isenberg. "Abnormalities of IgG glycosylation and immunological disorders" Wiley 1996; and Al-Rubaei "Cell Engineering: Glycosylation" Springer, 2002; each of which is incorporated by reference herein in its entirety.

In some embodiments, the antibody glycosylation state can be the antibody glycosylation state of an IgG antibody. For example, human IgG antibodies comprise a conserved N-glycosylation site within the CH2 domain of their Fc moieties, where the sugar side chain is attached to the asparagine 297 (Asn297) residue. The Asn297-linked carbohydrate chain consists of a common biantennary glycan structure of four N-acetylglucosamine (GlcNAc) and three mannose residues, with variable additions of fucose, galactose, sialic acid, and/or bisecting GlcNAc residues. Depending on the presence or absence of galactose on one or both arms of the glycan moiety, various antibody glycosylation states have been identified, e.g.: afucosylated branched glycoforms; 2-Galactose (G2), Fucosylated G2 (G2F), Fucosylated G2 with bisecting N-acetylglucosamine (G2FB);

In some embodiments, an antibody glycosylation state indicative of tuberculosis (TB) can be selected from the group consisting of decreased bi-galactosylated (G2): decreased fucosylated G2 (G2F); and decreased fucosylated G2 and bisected (G2FB). In some embodiments, an antibody glycosylation state indicative of tuberculosis (TB) can comprise decreased bi-galactosylated (G2): decreased fucosylated G2 (G2F); and decreased fucosylated G2 and bisected (G2FB). In some embodiments, an antibody glycosylation state indicative of tuberculosis (TB) can be selected from the group consisting of decreased bi-galactosylated (G2): decreased fucosylated G2 (G2F); decreased fucosylated G2 and bisected (G2FB); bisecting N-acetylglucosamine G0) G0B; fucosylated G0 with bisecting N-acetylglucosamine (G0FB); fucosylated G0 (G0F); and 1-galactose (G1). For further discussion of IgG glycosylation, see, e.g. Jefferis "Glycosylation of Natural and Recombinant Antibody Molecules" Chapter 26 in "Glycobiology and Medicine" Axford (ed.) Springer 2005; which is incorporated by reference herein in its entirety.

As described herein, the inventors have discovered that the antibody glycosylation state in a subject is altered by certain diseases and/or conditions, e.g. infection, a predisposition for and/or early stages of transplant rejection, or the competency of the subject to respond to (e.g. recover from and/or mount a successful immune response) an infection (e.g. flu responsive vs. flu non-responsive subjects). Accordingly, determining the antibody glycosylation state of a subject can permit, e.g., determining whether they have a disease and/or condition, are in need of treatment for a disease and/or condition; prognosing the outcome of a disease and/or condition; and/or permit treatment of the subject for a disease and/or condition.

Described herein are methods of determining antibody glycosylation states associated with a particular disease or condition, e.g. diagnostic of the presence of a disease or condition or prognostic of a particular disease or condition. For example, the antibody glycosylation states of a population of patients diagnosed as having a disease or condition can be assayed and compared to the antibody glycosylation states of a population of subjects not diagnosed as having a disease or condition and statistically significant differences in the states can be determined.

Assays for determining an antibody glycosylation state can comprise, e.g., the use of binding reagents specific for a particular glycosylation residue or pattern; a dLISA assay; mass spectroscopy; lectin-based assays; and/or a commercial available assay (see, e.g. GLYCO-PRO™ Sigma-Aldrich, St. Louis Mo.). An exemplary assay for glycan profiling of bulk IgG is described herein. Briefly: Bulk IgG can be purified and denatured, then treated with PNGase enzyme (NEB) to release N-linked glycans. Proteins can be precipitated in ice-cold ethanol and the glycan containing supernatants can be dried in a Centrivap. Dried glycans can be fluorescently labeled, e.g., with a 1:1 ratio of 50 mM APTS (8-aminoinopyrene-1,3,6-trisulfonic acid, Life Technologies) in 1.2 M citric acid and 1 M Sodium cyanoborohydride in tetrahydrofuran (Sigma-Aldrich) at 55° C. for 2 hours. Labeled glycans can be dissolved in ultrapure water and excess unbound APTS removed using Bio-Gel P-2 (Bio-rad) size exclusion columns. Samples can be sequenced, e.g., run with DNA ladder in Hi-Di formamide (Life Technologies) on an ABI 3130X1™ DNA sequencer. Data can be analyzed, e.g., using GeneMapper™ software and peaks were assigned based on migration of known standards and glycan digests. Peak area can be calculated and used to determine the relative percentage of each glycan structure.

In some embodiments, an antibody glycosylation state indicative of a disease and/or condition is an antibody glycosylation state that varies by a statistically significant amount from the antibody glycosylation state of a reference state. In some embodiments, the reference state can be the state in a healthy subject not diagnosed as having or not having the particular disease or condition. A reference state can be a previously determined state for an individual or an average state for a population of subjects (e.g. healthy subjects).

In some embodiments, the antibody glycosylation state of a subject can be monitored over time, e.g., the antibody glycosylation state of a subject can be assayed and/or determined at multiple points in time and changes in the state over time can be compared to a reference state and/or the earliest state of the subject. Changes in the antibody glycosylation state over time can indicate, e.g. progression and/or development of a disease or condition if the state changes to become more like a state indicative of a particular disease or condition or can indicate improvement and/or successful treatment of a disease or condition if the state changes to become more like a reference state or less like a state known to be indicative of a particular disease or condition.

In some embodiments, an antibody glycosylation state indicative of a disease can comprise a glycosylation level which varies by a statistically significant amount relative to the reference level. In some embodiments, an antibody glycosylation state indicative of a disease can comprise a galactosylation, sialation, and/or fucosylation level which varies by a statistically significant amount relative to a reference level. In some embodiments, an antibody glycosylation state indicative of a disease can comprise less glycosylation relative to the reference level. In some embodiments, an antibody glycosylation state indicative of a disease can comprise less galactosylation, sialation, and/or fucosylation relative to levels found in a normal individual.

In some embodiments, an antibody glycosylation state indicative of a disease and/or condition can be marked by one or more different glycan structures relative to a reference state. In some embodiments, an antibody glycosylation state indicative of a disease and/or condition can be marked by one or more different glycan structures relative to a healthy subject. In some embodiments, an antibody glycosylation state indicative of an active disease and/or condition can be marked by one or more different glycan structures relative to an antibody glycosylation state in a subject with a latent disease and/or condition.

In some embodiments, the antibody glycosylation state can comprise glycans attached to antibody Fc domains, e.g. as opposed to glycans attached at other positions of an antibody. In some embodiments, the antibody glycosylation state can consist of glycans attached to antibody Fc domains, e.g. as opposed to glycans attached at other positions of an antibody. In some embodiments, the antibody glycosylation state indicative of the disease can be a decreased presence of afucosylated branched glycoforms on bulk IgG.

In some embodiments, the antibody glycosylation state indicative of the disease can comprise an inflamed antibody Fc-domain. As used herein, an "inflamed" antibody Fc-domain refers to an antibody Fc-domain marked by less galactose and less sialic acid as compared to a reference level, e.g. a level present in a subject with no symptoms or signs of inflammation, or in the same subject prior to development of signs or symptoms of inflammation.

In some embodiments, an antibody glycosylation state can be the antibody glycosylation state of one or more IgG antibodies. In some embodiments, the antibody glycosylation state can be the antibody glycosylation state of one or more IgG antibodies present in the plasma of the subject.

In some embodiments, an antibody glycosylation state can be the antibody glycosylation state of one or more antibodies that specifically bind antigens associated with the disease or condition. Antigens associated with the disease or condition are known in the art and can include, e.g., microbial antigens, e.g. biomolecules produced by *Mycobacterium tuberculosis* or a flu virus.

Antibody glycosylation states indicative of a disease or condition can be a component of the pathology of that disease or condition and/or contribute to an undesirable immune response to the disease or condition. Accordingly, in one aspect, described herein is a method of treating a disease or condition that comprises administering a therapeutically effective dose of an antibody with an antibody glycosylation state that is not statistically significantly different than a reference state. In some embodiments, the treatment can comprise administering an inhibitor of antibodies with an antibody glycosylation state indicative of a disease or condition, e.g. an inhibitor can be an antibody reagent that specifically binds to antibodies with a glycosylation state indicative of a disease or condition.

Exemplary antibody glycosylation states indicative of particular disease or conditions are described herein. For example:

In some embodiments, an antibody glycosylation state indicative of tuberculosis (TB) can be selected from the group consisting of decreased bi-galactosylated (G2): decreased fucosylated G2 (G2F); and decreased fucosylated G2 and bisected (G2FB). In some embodiments, an antibody glycosylation state indicative of tuberculosis (TB) can comprise decreased bi-galactosylated (G2): decreased fucosylated G2 (G2F); and decreased fucosylated G2 and bisected (G2FB). In some embodiments, an antibody glycosylation state indicative of tuberculosis (TB) can be selected from the group consisting of decreased bi-galactosylated (G2): decreased fucosylated G2 (G2F); decreased fucosylated G2 and bisected (G2FB); and bisecting N-acetylglucosamine G0) G0B.

In some embodiments, an antibody glycosylation state indicative of transplant rejection can be selected from the group consisting of: increased fucosylated G0 with bisecting N-acetylglucosamine (G0FB) and increased fucosylated G0 (G0F). In some embodiments, an antibody glycosylation state indicative of transplant rejection can comprise increased G0F and G0FB but not increased (bisecting N-acetylglucosamine G0) G0B.

In some embodiments, an antibody glycosylation state indicative of flu non-responsiveness (e.g., a subject that will not mount an appropriate and/or successful immune response to the flu and/or a subject that will require medical intervention to survive a flu infection can be selected from the group consisting of: increased 1-galactose (G1); increased G0B and decreased G0F. In some embodiments, an antibody glycosylation state indicative of flu non-responsiveness can comprise increased G1 and G0B but not increased G0F.

In some embodiments, treatment of flu non-responsiveness can comprise decreasing the level and/or activity of antibodies with a G1 and/or G0B glycosylation state in the subject, e.g., by administering antibodies that block the Fc-binding proteins that bind to the G1 and/or G0B structures present on antibodies and/or administer an adjuvant that can bias a vaccine-induced immune response away from the G1/G0B anti-inflammatory effects.

Treatments for, e.g., tuberculosis, transplant rejection, or flu non-responsiveness are known in the art. By way of non-limiting example, treatments for tuberculosis can include antibiotics (e.g. rifampicin, isoniazid, pyrazinamide, ethambutol, and bedaquiline). By way of non-limiting example, treatments for transplant rejection can include immunosuppressants (e.g., corticosteroids, calcineurin inhibitors, anti-proliferatives, and mTOR inhibitors) antibody-based treatments (e.g., monoclonal anti-IL-2Rap1ha receptor inhibitors (e.g. basiliximab and daclizumab), polyclonal anti-T-cell antibodies anti-CD20 antibodies (e.g. rituximab)); blood transfer, marrow transplant. By way of non-limiting example, treatments for flu non-responsiveness can include antivirals (e.g. neuraminidase inhibitors (e.g., oseltamivir and zanamivir) and M2 protein inhibitors (e.g. adamantane inhibitors)). As described elsewhere herein, diseases and conditions can be treated by administering antibodies (e.g. IgG and/or antibodies that specifically bind an antigen associated with the disease or condition) with an antibody glycosylation state that is associated with a healthy subject, as opposed to an antibody glycosylation state that is associated with a subject having the disease or condition. As described elsewhere herein, diseases and conditions can be treated by administering an agent that inhibits the level and/or activity of antibodies having an antibody glycosylation state characteristic of the disease or condition.

The term "sample" or "test sample" as used herein denotes a sample taken or isolated from a biological organism, e.g., a tumor sample from a subject. Exemplary biological samples include, but are not limited to, a biofluid sample; serum; plasma; urine; saliva; a tumor sample; a tumor biopsy and/or tissue sample etc. The term also includes a mixture of the above-mentioned samples. The term "test sample" also includes untreated or pretreated (or pre-processed) biological samples. In some embodiments, a test sample can comprise cells from subject. In some embodiments, a test sample can be a plasma and/or blood sample.

The test sample can be obtained by removing a sample from a subject, but can also be accomplished by using previously isolated samples (e.g. isolated at a prior timepoint and isolated by the same or another person). In addition, the test sample can be freshly collected or a previously collected sample.

In some embodiments, the test sample can be an untreated test sample. As used herein, the phrase "untreated test sample" refers to a test sample that has not had any prior sample pre-treatment except for dilution and/or suspension in a solution. Exemplary methods for treating a test sample include, but are not limited to, centrifugation, filtration, sonication, homogenization, heating, freezing and thawing, and combinations thereof. In some embodiments, the test sample can be a frozen test sample, e.g., a frozen tissue. The frozen sample can be thawed before employing methods, assays and systems described herein. After thawing, a frozen sample can be centrifuged before being subjected to methods, assays and systems described herein. In some embodiments, the test sample is a clarified test sample, for example, by centrifugation and collection of a supernatant comprising the clarified test sample. In some embodiments, a test sample can be a pre-processed test sample, for example, supernatant or filtrate resulting from a treatment selected from the group consisting of centrifugation, filtration, thawing, purification, and any combinations thereof. In some embodiments, the test sample can be treated with a chemical and/or biological reagent. Chemical and/or biological reagents can be employed to protect and/or maintain the stability of the sample, including biomolecules (e.g., nucleic acid and protein) therein, during processing. One exemplary reagent is a protease inhibitor, which is generally used to protect or maintain the stability of protein during processing. The skilled artisan is well aware of methods and processes appropriate for pre-processing of biological samples required for determination of the presence of a sensitizing mutation as described herein.

In some embodiments, the methods, assays, and systems described herein can further comprise a step of obtaining a test sample from a subject. In some embodiments, the subject can be a human subject.

In one aspect, described herein is a pharmaceutical composition comprising one or more antibodies (e.g. IgG and/or antibodies that specifically bind an antigen associated with a particular disease or condition) with an antibody glycosylation state that is associated with a healthy subject, as opposed to an antibody glycosylation state that is associated with a subject having the disease or condition. In one aspect, described herein is a pharmaceutical composition comprising an agent that inhibits the level and/or activity of antibodies having an antibody glycosylation state characteristic of the disease or condition, e.g. an antibody specific for at least one aspect of an antibody glycosylation state characteristic of the disease or condition.

The present invention is also directed to a kit to diagnose and/or treat infection. The kit is an assemblage of materials or components, including at least one of the inventive compositions. Thus, in some embodiments the kit contains a composition including secondary antibodies used in determining the degree of glycosylation, as described above.

The exact nature of the components configured in the inventive kit depends on its intended purpose. For example, some embodiments are configured for the purpose of treating tuberculosis. In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to diagnose the state of infection at the point of care. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well known methods, preferably to provide a sterile, contaminant-free environment. As used herein, the term "package" refers to a suitable solid matrix or material such as glass, plastic, paper, foil, and the like, capable of holding the individual kit components. The packaging material generally has an external label which indicates the contents and/or purpose of the kit and/or its components.

As readily apparent to one of skill in the art, the present invention may be used in conjunction with the diagnosis and treatment of any number of conditions and diseases related to antigen specific immune and/or inflammatory response, and the invention is in no way limited to tuberculosis or infection related to elderly flu, syphilis, legionella, lyme disease and CMV reactivation. Similarly, there are several methods that may be used for biophysical profiling of antigen/disease specific antibodies and the present invention is not limited to only analyzing the degree of galactosylation, fucosylation and sialation of the antibody when determining the degree of glycosylation as a measure of activity of a condition or infection. For example, in one embodiment, the present invention may generally examine modulation in the recruitment of innate immune effector cells as a means of diagnosing active tuberculosis in a patient.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Subjects having tuberculosis (e.g., an Mtb infection) or suffering from the symptoms of an Mtb infection can be identified by a physician using current methods of diagnosing Mtb infections. Symptoms and/or complications of Mtb infection useful in making such diagnoses include, but are not limited to chronic cough, blood-tinged sputum, fever, chest pain, pallor, chills, fatigue, night sweats, and weight loss. If Mtb infection spreads to organs other than the lungs, a variety of symptoms can arise that are specific to the particular organ infected. Test and diagnostic tools that may aid in a diagnosis of Mtb infection include, but are not limited to x-rays, chest x-rays, tuberculin skin test, blood tests, microscopic examination of bodily fluids, microbiological culture of bodily fluids, chest photofluorography, the Ziehl-Neelsen stain, auramine-rhodamine stain, fluorescent microscopy, PCR tests, amplified *Mycobacterium tuberculosis* direct test (MTD, Gen-Probe) or an interferon gamma release assay (IGRA).

Subjects can have an elevated risk of having or developing an Mtb infection for a number of reasons. Risk factors that predispose a subject to Mtb include, but are not limited to, certain polymorphisms in the IL12B gene, a family history of Mtb infection, treatment with immunosuppressive drugs, cigarette use, treatment for rheumatoid arthritis with anti-TNFα therapy, illegal drug use, low BMI, AIDS, silicosis, exposure to silica particles, diabetes mellitus, jejunoileal bypass, renal and cardiac transplantation, carcinoma of the head or neck, other neoplasms and incarceration in a prison.

The compositions and methods described herein can be administered to a subject having or diagnosed as having, e.g. tuberculosis. In some embodiments, the methods described herein comprise administering an effective amount of compositions described herein to a subject in order to alleviate a symptom of a disease or condition. As used herein, "alleviating a symptom of a disease or condition" is ameliorating any condition or symptom associated with the disease or condition. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, topical, injection, or intratumoral administration. Administration can be local or systemic.

The term "effective amount" as used herein refers to the amount of a composition needed to alleviate at least one or more symptom of the disease or disorder, and relates to a sufficient amount of pharmacological composition to provide the desired effect. The term "therapeutically effective amount" therefore refers to an amount of a composition that is sufficient to provide a particular effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for bacterial and/or viral titer, among others. The dosage can be determined by a physician and adjusted, as necessary, to suit observed effects of the treatment.

In some embodiments, the technology described herein relates to a pharmaceutical composition as described herein, and optionally a pharmaceutically acceptable carrier. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent, as described herein.

In some embodiments, the pharmaceutical composition can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms as disclosed within are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of a composition as disclosed herein can also be incorporated into the parenteral dosage forms of the disclosure, including conventional and controlled-release parenteral dosage forms.

Pharmaceutical compositions can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia Pa. (2005).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, the composition can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos.: 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

The methods described herein can further comprise administering a second agent and/or treatment to the subject, e.g. as part of a combinatorial therapy. By way of non-limiting example, a subject with tuberculosis can be further administered an antibiotic or a subject likely to experience transplant rejection can be further administered an immunosuppressant.

In certain embodiments, an effective dose of a composition as described herein can be administered to a patient once. In certain embodiments, an effective dose of a composition can be administered to a patient repeatedly. For systemic administration, subjects can be administered a therapeutic amount of a composition, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. bacterial and/or viral titers by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the active ingredient. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition can be administered over a period of time, such as over a 5 minute, 10 minute, 15 minute, 20 minute, or 25 minute period.

The dosage ranges for the administration of the compositions described herein, according to the methods described herein depend upon, for example, the form of the composition, its potency, and the extent to which symptoms, markers, or indicators of a condition described herein are desired to be reduced, for example the percentage reduction desired for a symptom or the extent to which, for example, successful immune responses are desired to be induced. The dosage should not be so large as to cause adverse side effects. Generally, the dosage will vary with the age, condition, and sex of the patient and can be determined by one of skill in the art. The dosage can also be adjusted by the individual physician in the event of any complication.

The efficacy of a composition in, e.g. the treatment of a condition described herein, or to induce a response as described herein can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g. bacterial and/or viral levels. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response. It is well within the ability of one skilled in the art to monitor efficacy of administration and/or treatment by measuring any one of such parameters, or any combination of parameters. Efficacy can be assessed in animal models of a condition described herein, for example treatment of tuberculosis. When using an experimental animal model, efficacy of treatment is evidenced when a statistically significant change in a marker is observed, e.g. a decreased in the presence of Mycobacterium in the subject, or a progression towards latent instead of active disease.

In vitro and animal model assays are provided herein which allow the assessment of a given dose of a composition. By way of non-limiting example, the effects of a dose of a composition can be assessed by administering the composition to an animal model of tuberculosis, e.g. a mouse infected with Mycobacterium.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, an "increase" is a statistically significant increase in such level.

As used herein, a "subject" means a human or animal. Usually the animal is a vertebrate such as a primate, rodent, domestic animal or game animal. Primates include chimpanzees, cynomolgous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of the disease or condition. A subject can be male or female.

A subject can be one who has been previously diagnosed with or identified as suffering from or having a condition in need of treatment (e.g. tuberculosis) or one or more complications related to such a condition, and optionally, have already undergone treatment for the disease or condition or the one or more complications related to the disease or condition. Alternatively, a subject can also be one who has not been previously diagnosed as having the disease or condition or one or more complications related to the disease or condition. For example, a subject can be one who exhibits one or more risk factors for the disease or condition or one or more complications related to the disease or condition or a subject who does not exhibit risk factors.

A "subject in need" of treatment for a particular condition can be a subject having that condition, diagnosed as having that condition, or at risk of developing that condition.

As used herein an "antibody" refers to IgG, IgM, IgA, IgD or IgE molecules or antigen-specific antibody fragments thereof (including, but not limited to, a Fab, F(ab')$_2$, Fv, disulphide linked Fv, scFv, single domain antibody, closed conformation multispecific antibody, disulphide-linked scfv, diabody), whether derived from any species that naturally produces an antibody, or created by recombinant DNA technology; whether isolated from serum, B-cells, hybridomas, transfectomas, yeast or bacteria.

As described herein, an "antigen" is a molecule that is bound by a binding site on an antibody agent. Typically, antigens are bound by antibody ligands and are capable of raising an antibody response in vivo. An antigen can be a polypeptide, protein, nucleic acid or other molecule or portion thereof. The term "antigenic determinant" refers to an epitope on the antigen recognized by an antigen-binding molecule, and more particularly, by the antigen-binding site of said molecule.

As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, and domain antibodies (dAb) fragments (see, e.g. de Wildt et al., Eur J. Immunol. 1996; 26(3):629-39; which is incorporated by reference herein in its entirety)) as well as complete antibodies. An antibody can have the structural features of IgA, IgG, IgE, IgD, IgM (as well as subtypes and combinations thereof). Antibodies can be from any source, including mouse, rabbit, pig, rat, and primate (human and non-human primate) and primatized antibodies. Antibodies also include midibodies, humanized antibodies, chimeric antibodies, and the like.

The VH and VL regions can be further subdivided into regions of hypervariability, termed "complementarity determining regions" ("CDR"), interspersed with regions that are more conserved, termed "framework regions" ("FR"). The extent of the framework region and CDRs has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917; which are incorporated by reference herein in their entireties). Each VH and VL is typically composed of three CDRs and four FRs, arranged from amino-terminus to carboxy-terminus in the following order: FR1, CDR1, FR2, CDR2, FR3, CDR3, FR4.

The terms "antigen-binding fragment" or "antigen-binding domain", which are used interchangeably herein are used to refer to one or more fragments of a full length antibody that retain the ability to specifically bind to a target of interest. Examples of binding fragments encompassed within the term "antigen-binding fragment" of a full length antibody include (i) a Fab fragment, a monovalent fragment consisting of the VL, VH, CL and CH1 domains; (ii) a F(ab')2 fragment, a bivalent fragment including two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment (Ward et al., (1989) Nature 341:544-546; which is incorporated by reference herein in its entirety), which consists of a VH or VL domain; and (vi) an isolated complementarity determining region (CDR) that retains specific antigen-binding functionality. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). See e.g., U.S. Pat. Nos. 5,260,203, 4,946,778, and 4,881,175; Bird et al. (1988) Science 242:423-426; and Huston et al. (1988) Proc. Natl. Acad. Sci. USA 85:5879-5883. Antibody fragments can be obtained using any appropriate technique including conventional techniques known to those of skill in the art. The term "monospecific antibody" refers to an antibody that displays a single binding specificity and affinity for a particular target, e.g., epitope. This term includes a "monoclonal antibody" or "monoclonal antibody composition," which as used herein refer to a preparation of antibodies or fragments thereof of single molecular composition, irrespective of how the antibody was generated.

A further kind of antibody reagent is an intrabody i.e. an intracellular antibody (See, generally, Hood et al., Immunology, Benjamin, N.Y., 2ND ed. (1984), Harlow and Lane, Antibodies. A Laboratory Manual, Cold Spring Harbor Laboratory (1988) and Hunkapiller and Hood, Nature, 323, 15-16 (1986), which are incorporated herein by reference). Intrabodies work within the cell and bind intracellular protein. Intrabodies can include whole antibodies or antibody binding fragments thereof, e.g. single Fv, Fab and F(ab)'2, etc. Methods for intrabody production are well known to those of skill in the art, e.g. as described in WO 2002/086096. Antibodies will usually bind with at least a KD of about 1 mM, more usually at least about 300 µM, typically at least about 10 µM, more typically at least about 30 µM, preferably at least about 10 µM, and more preferably at least about 3 µM or better).

As used herein, the term "specific binding" refers to a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third nontarget entity.

Avidity is the measure of the strength of binding between an antigen-binding molecule (such as an antibody reagent described herein) and the pertinent antigen. Avidity is related to both the affinity between an antigenic determinant and its antigen binding site on the antigen-binding molecule, and the number of pertinent binding sites present on the antigen-binding molecule. Typically, antigen-binding proteins (such as an antibody reagent described herein) will bind to their cognate or specific antigen with a dissociation constant ($K_D$ of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles). Any $K_D$ value greater than $10^{-4}$ mol/liter (or any $K_A$ value lower than $10^4$ M$^{-1}$) is generally considered to indicate non-specific binding. The $K_D$ for biological interactions which are considered meaningful (e.g. specific) are typically in the range of $10^{-10}$ M (0.1 nM) to $10^{-5}$ M (10000 nM). The stronger an interaction is, the lower is its $K_D$. Preferably, a binding site on an antibody reagent described herein will bind to the desired antigen with an affinity less than 500 nM, preferably less than 200 nM, more preferably less than 10 nM, such as less than 500 pM. Specific binding of an antibody reagent to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as other techniques as mentioned herein.

Accordingly, as used herein, "selectively binds" or "specifically binds" refers to the ability of an agent (e.g. an antibody reagent) described herein to bind to a target with a $K_D$ $10^{-5}$ M (10000 nM) or less, e.g., $10^{-6}$ M or less, $10^{-7}$ M or less, $10^{-8}$ M or less, $10^{-9}$ M or less, $10^{-10}$ M or less, $10^{-11}$ M or less, or $10^{-12}$ M or less. For example, if an agent described herein binds to a first peptide comprising a target antigen or an epitope thereof with a $K_D$ of $10^{-5}$ M or lower, but not to another randomly selected peptide, then the agent is said to specifically bind the first peptide. Specific binding can be influenced by, for example, the affinity and avidity of the agent and the concentration of the agent. The person of ordinary skill in the art can determine appropriate conditions under which an agent selectively bind the targets using any suitable methods, such as titration of an agent in a suitable cell and/or a peptide binding assay.

Traditionally, monoclonal antibodies have been produced as native molecules in murine hybridoma lines. In addition to that technology, the methods and compositions described herein provide for recombinant DNA expression of monoclonal antibodies. This allows the production of humanized antibodies as well as a spectrum of antibody derivatives and fusion proteins in a host species of choice. The production of antibodies in bacteria, yeast, transgenic animals and chicken eggs are also alternatives to hybridoma-based production systems. The main advantages of transgenic animals are potential high yields from renewable sources.

As used herein, an "epitope" can be formed both from contiguous amino acids, or noncontiguous amino acids juxtaposed by folding of a protein. Epitopes formed from contiguous amino acids are typically retained on exposure to denaturing solvents, whereas epitopes formed by folding are typically lost on treatment with denaturing solvents. An epitope typically includes at least 3, and more usually, at least 5, about 9, or about 8-10 amino acids in a unique spatial conformation. An "epitope" includes the unit of structure conventionally bound by an immunoglobulin $V_H/V_L$ pair. Epitopes define the minimum binding site for an antibody, and thus represent the target of specificity of an antibody. In the case of a single domain antibody, an epitope represents the unit of structure bound by a variable domain in isolation. The terms "antigenic determinant" and "epitope" can also be used interchangeably herein.

Nucleic acid molecules encoding amino acid sequence variants of antibodies are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody. A nucleic acid sequence encoding at least one antibody, portion or polypeptide as described herein can be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed, e.g., by Maniatis et al., Molecular Cloning, Lab. Manual (Cold Spring Harbor Lab. Press, N.Y., 1982 and 1989), and Ausubel, 1987, 1993, and can be used to construct nucleic acid sequences which encode a monoclonal antibody molecule or antigen binding region thereof. A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression as peptides or antibody portions in recoverable amounts. The precise nature of the regulatory regions needed for gene expression may vary from organism to organism, as is well known in the analogous art. See, e.g., Sambrook et al., 1989; Ausubel et al., 1987-1993.

Accordingly, the expression of an antibody or antigen-binding portion thereof as described herein can occur in either prokaryotic or eukaryotic cells. Suitable hosts include bacterial or eukaryotic hosts, including yeast, insects, fungi, bird and mammalian cells either in vivo, or in situ, or host cells of mammalian, insect, bird or yeast origin. The mammalian cell or tissue can be of human, primate, hamster, rabbit, rodent, cow, pig, sheep, horse, goat, dog or cat origin, but any other mammalian cell may be used. Further, by use of, for example, the yeast ubiquitin hydrolase system, in vivo synthesis of ubiquitin-transmembrane polypeptide fusion proteins can be accomplished. The fusion proteins so produced can be processed in vivo or purified and processed in vitro, allowing synthesis of an antibody or portion thereof as described herein with a specified amino terminus sequence. Moreover, problems associated with retention of initiation codon-derived methionine residues in direct yeast (or bacterial) expression may be avoided. Sabin et al., 7 Bio/Technol. 705 (1989); Miller et al., 7 Bio/Technol. 698 (1989). Any of a series of yeast gene expression systems incorporating promoter and termination elements from the actively expressed genes coding for glycolytic enzymes produced in large quantities when yeast are grown in media rich in glucose can be utilized to obtain recombinant antibodies or antigen-binding portions thereof. Known glycolytic genes can also provide very efficient transcriptional control signals. For example, the promoter and terminator signals of the phosphoglycerate kinase gene can be utilized.

Production of antibodies or antigen-binding portions thereof as described herein can be achieved in insects, for example, by infecting the insect host with a baculovirus engineered to express a transmembrane polypeptide by methods known to those of skill in the art. See Ausubel et al., 1987, 1993.

In some embodiments, the introduced nucleotide sequence is incorporated into a plasmid or viral vector capable of autonomous replication in the recipient host. Any of a wide variety of vectors can be employed for this purpose and are known and available to those of ordinary skill in the art. See, e.g., Ausubel et al., 1987, 1993. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Example prokaryotic vectors known in the art include plasmids such as those capable of replication in *E. coli*, for example. Other gene expression elements useful for the expression of cDNA encoding antibodies or antigen-binding portions thereof include, but are not limited to (a) viral transcription promoters and their enhancer elements, such as the SV40 early promoter (Okayama et al., 3 Mol. Cell. Biol. 280 (1983)), Rous sarcoma virus LTR (Gorman et al., 79 PNAS 6777 (1982)), and Moloney murine leukemia virus LTR (Grosschedl et al., 41 Cell 885 (1985)); (b) splice regions and polyadenylation sites such as those derived from the SV40 late region (Okayarea et al., 1983), and (c) polyadenylation sites such as in SV40 (Okayama et al., 1983). Immunoglobulin cDNA genes can be expressed as described by Liu et al., infra, and Weidle et al., 51 Gene 21 (1987), using as expression elements the SV40 early promoter and its enhancer, the mouse immunoglobulin H chain promoter enhancers, SV40 late region mRNA splicing, rabbit S-globin intervening sequence, immunoglobulin and rabbit S-globin polyadenylation sites, and SV40 polyadenylation elements.

For immunoglobulin genes comprised of part cDNA, part genomic DNA (Whittle et al., 1 Protein Engin. 499 (1987)), the transcriptional promoter can be human cytomegalovirus, the promoter enhancers can be cytomegalovirus and mouse/human immunoglobulin, and mRNA splicing and polyadenylation regions can be the native chromosomal immunoglobulin sequences.

In some embodiments, for expression of cDNA genes in rodent cells, the transcriptional promoter is a viral LTR sequence, the transcriptional promoter enhancers are either or both the mouse immunoglobulin heavy chain enhancer and the viral LTR enhancer, the splice region contains an intron of greater than 31 bp, and the polyadenylation and transcription termination regions are derived from the native chromosomal sequence corresponding to the immunoglobulin chain being synthesized. In other embodiments, cDNA sequences encoding other proteins are combined with the above-recited expression elements to achieve expression of the proteins in mammalian cells.

Each fused gene is assembled in, or inserted into, an expression vector. Recipient cells capable of expressing the chimeric immunoglobulin chain gene product are then transfected singly with an antibody, antigen-binding portion thereof, or chimeric H or chimeric L chain-encoding gene, or are co-transfected with a chimeric H and a chimeric L chain gene. The transfected recipient cells are cultured under conditions that permit expression of the incorporated genes and the expressed immunoglobulin chains or intact antibodies or fragments are recovered from the culture.

In some embodiments, the fused genes encoding the antibody, antigen-binding fragment thereof, or chimeric H and L chains, or portions thereof are assembled in separate expression vectors that are then used to co-transfect a recipient cell. Each vector can contain two selectable genes, a first selectable gene designed for selection in a bacterial system and a second selectable gene designed for selection in a eukaryotic system, wherein each vector has a different pair of genes. This strategy results in vectors which first direct the production, and permit amplification, of the fused genes in a bacterial system. The genes so produced and amplified in a bacterial host are subsequently used to co-transfect a eukaryotic cell, and allow selection of a co-transfected cell carrying the desired transfected genes. Non-limiting examples of selectable genes for use in a bacterial system are the gene that confers resistance to ampicillin and the gene that confers resistance to chloramphenicol. Selectable genes for use in eukaryotic transfectants include the xanthine guanine phosphoribosyl transferase gene (designated gpt) and the phosphotransferase gene from Tn5 (designated neo). Alternatively the fused genes encoding chimeric H and L chains can be assembled on the same expression vector.

For transfection of the expression vectors and production of the chimeric, humanized, or composite human antibodies described herein, the recipient cell line can be a myeloma cell. Myeloma cells can synthesize, assemble and secrete immunoglobulins encoded by transfected immunoglobulin genes and possess the mechanism for glycosylation of the immunoglobulin. For example, in some embodiments, the recipient cell is the recombinant Ig-producing myeloma cell SP2/0 (ATCC #CRL 8287). SP2/0 cells produce only immunoglobulin encoded by the transfected genes. Myeloma cells can be grown in culture or in the peritoneal cavity of a mouse, where secreted immunoglobulin can be obtained from ascites fluid. Other suitable recipient cells include lymphoid cells such as B lymphocytes of human or non-human origin, hybridoma cells of human or non-human origin, or interspecies heterohybridoma cells.

An expression vector carrying a chimeric, humanized, or composite human antibody construct, antibody, or antigen-binding portion thereof as described herein can be introduced into an appropriate host cell by any of a variety of suitable means, including such biochemical means as transformation, transfection, conjugation, protoplast fusion, calcium phosphate-precipitation, and application with polycations such as diethylaminoethyl (DEAE) dextran, and such mechanical means as electroporation, direct microinjection, and microprojectile bombardment. Johnston et al., 240 Science 1538 (1988), as known to one of ordinary skill in the art.

Yeast provides certain advantages over bacteria for the production of immunoglobulin H and L chains. Yeasts carry out post-translational peptide modifications including glycosylation. A number of recombinant DNA strategies exist that utilize strong promoter sequences and high copy number plasmids which can be used for production of the desired proteins in yeast. Yeast recognizes leader sequences of cloned mammalian gene products and secretes peptides bearing leader sequences (i.e., pre-peptides). Hitzman et al., 11th Intl. Conf. Yeast, Genetics & Molec. Biol. (Montpelier, France, 1982).

Yeast gene expression systems can be routinely evaluated for the levels of production, secretion and the stability of antibodies, and assembled chimeric, humanized, or composite human antibodies, portions and regions thereof. Any of a series of yeast gene expression systems incorporating promoter and termination elements from the actively expressed genes coding for glycolytic enzymes produced in large quantities when yeasts are grown in media rich in glucose can be utilized. Known glycolytic genes can also provide very efficient transcription control signals. For example, the promoter and terminator signals of the phosphoglycerate kinase (PGK) gene can be utilized. A number of approaches can be taken for evaluating optimal expression plasmids for the expression of cloned immunoglobulin cDNAs in yeast. See II DNA Cloning 45, (Glover, ed., IRL Press, 1985) and e.g., U.S. Publication No. US 2006/0270045 A1.

Bacterial strains can also be utilized as hosts for the production of the antibody molecules or peptides described herein, *E. coli* K12 strains such as *E. coli* W3110 (ATCC 27325), *Bacillus* species, enterobacteria such as *Salmonella typhimurium* or *Serratia marcescens*, and various *Pseudomonas* species can be used. Plasmid vectors containing replicon and control sequences which are derived from species compatible with a host cell are used in connection with these bacterial hosts. The vector carries a replication site, as well as specific genes which are capable of providing phenotypic selection in transformed cells. A number of approaches can be taken for evaluating the expression plasmids for the production of chimeric, humanized, or composite humanized antibodies and fragments thereof encoded by the cloned immunoglobulin cDNAs or CDRs in bacteria (see Glover, 1985; Ausubel, 1987, 1993; Sambrook, 1989; Colligan, 1992-1996).

Host mammalian cells can be grown in vitro or in vivo. Mammalian cells provide post-translational modifications to immunoglobulin protein molecules including leader peptide removal, folding and assembly of H and L chains, glycosylation of the antibody molecules, and secretion of functional antibody protein.

In some embodiments, one or more antibodies or antibody reagents thereof as described herein can be produced in vivo in an animal that has been engineered or transfected with one or more nucleic acid molecules encoding the polypeptides, according to any suitable method.

In some embodiments, an antibody or antibody reagent as described herein is produced in a cell-free system. Nonlimiting exemplary cell-free systems are described, e.g., in Sitaraman et al., Methods Mol. Biol. 498: 229-44 (2009); Spirin, Trends Biotechnol. 22: 538-45 (2004); Endo et al., Biotechnol. Adv. 21: 695-713 (2003).

Many vector systems are available for the expression of cloned H and L chain genes in mammalian cells (see Glover, 1985). Different approaches can be followed to obtain complete $H_2L_2$ antibodies. As discussed above, it is possible to co-express H and L chains in the same cells to achieve intracellular association and linkage of H and L chains into complete tetrameric $H_2L_2$ antibodies or antigen-binding portions thereof. The co-expression can occur by using either the same or different plasmids in the same host. Genes for both H and L chains or portions thereof can be placed into the same plasmid, which is then transfected into cells, thereby selecting directly for cells that express both chains. Alternatively, cells can be transfected first with a plasmid encoding one chain, for example the L chain, followed by transfection of the resulting cell line with an H chain plasmid containing a second selectable marker. Cell lines producing antibodies, antigen-binding portions thereof and/or $H_2L_2$ molecules via either route could be transfected with plasmids encoding additional copies of peptides, H, L, or H plus L chains in conjunction with additional selectable markers to generate cell lines with enhanced properties, such as higher production of assembled $H_2L_2$ antibody molecules or enhanced stability of the transfected cell lines.

Additionally, plants have emerged as a convenient, safe and economical alternative main-stream expression systems for recombinant antibody production, which are based on large scale culture of microbes or animal cells. Antibodies can be expressed in plant cell culture, or plants grown conventionally. The expression in plants may be systemic, limited to susb-cellular plastids, or limited to seeds (endosperms). See, e.g., U.S. Patent Pub. No. 2003/0167531; U.S. Pat. Nos. 6,080,560; 6,512,162; WO 0129242. Several plant-derived antibodies have reached advanced stages of development, including clinical trials (see, e.g., Biolex, N.C.).

In some aspects, provided herein are methods and systems for the production of a humanized antibody, which is prepared by a process which comprises maintaining a host transformed with a first expression vector which encodes the light chain of the humanized antibody and with a second expression vector which encodes the heavy chain of the humanized antibody under such conditions that each chain is expressed and isolating the humanized antibody formed by assembly of the thus-expressed chains. The first and second expression vectors can be the same vector. Also provided herein are DNA sequences encoding the light chain or the heavy chain of the humanized antibody; an expression vector which incorporates a said DNA sequence; and a host transformed with a said expression vector.

Generating a humanized antibody from the sequences and information provided herein can be practiced by those of ordinary skill in the art without undue experimentation. In one approach, there are four general steps employed to humanize a monoclonal antibody, see, e.g., U.S. Pat. Nos. 5,585,089; 6,835,823; 6,824,989. These are: (1) determining the nucleotide and predicted amino acid sequence of the starting antibody light and heavy variable domains; (2) designing the humanized antibody, i.e., deciding which antibody framework region to use during the humanizing process; (3) the actual humanizing methodologies/techniques; and (4) the transfection and expression of the humanized antibody.

Usually the CDR regions in humanized antibodies and human antibody variants are substantially identical, and more usually, identical to the corresponding CDR regions in the mouse or human antibody from which they were derived. Although not usually desirable, it is sometimes possible to make one or more conservative amino acid substitutions of CDR residues without appreciably affecting the binding affinity of the resulting humanized immunoglobulin or human antibody variant. Occasionally, substitutions of CDR regions can enhance binding affinity.

In addition, techniques developed for the production of "chimeric antibodies" (see Morrison et al., Proc. Natl. Acad. Sci. 81:851-855 (1984); Neuberger et al., Nature 312:604-608 (1984); Takeda et al., Nature 314:452-454 (1985); which are incorporated by reference herein in their entireties) by splicing genes from a mouse, or other species, antibody molecule of appropriate antigen specificity together with genes from a human antibody molecule of appropriate biological activity can be used. A chimeric antibody is a molecule in which different portions are derived from different animal species, such as those having a variable region derived from a murine monoclonal antibody and a human immunoglobulin constant region, e.g., humanized antibodies. The variable segments of chimeric antibodies are typically linked to at least a portion of an immunoglobulin constant region (Fc), typically that of a human immunoglobulin. Human constant region DNA sequences can be isolated in accordance with well-known procedures from a variety of human cells, such as immortalized B-cells (WO 87/02671; which is incorporated by reference herein in its entirety). The antibody can contain both light chain and heavy chain constant regions. The heavy chain constant region can include CH1, hinge, CH2, CH3, and, sometimes, CH4 regions. For therapeutic purposes, the CH2 domain can be deleted or omitted.

Alternatively, techniques described for the production of single chain antibodies (see, e.g. U.S. Pat. No. 4,946,778; Bird, Science 242:423-42 (1988); Huston et al., Proc. Natl. Acad. Sci. USA 85:5879-5883 (1988); and Ward et al., Nature 334:544-54 (1989); which are incorporated by reference herein in their entireties) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* can also be used (see, e.g. Skerra et al., Science 242:1038-1041 (1988); which is incorporated by reference herein in its entirety).

Chimeric, humanized and human antibodies are typically produced by recombinant expression. Recombinant polynucleotide constructs typically include an expression control sequence operably linked to the coding sequences of antibody chains, including naturally-associated or heterologous promoter regions. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the cross-reacting antibodies. These expression vectors are typically replicable in the host organisms either as episomes or as an integral part of the host chromosomal DNA. Commonly, expression vectors contain selection markers, e.g., ampicillin-resistance or hygromycin-resistance, to permit detection of those cells transformed with the desired DNA sequences. *E. coli* is one prokaryotic host particularly useful for cloning the DNA sequences. Microbes, such as yeast are also useful for expression. *Saccharomyces* is a preferred yeast host, with suitable vectors having expression control sequences, an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization. Mammalian cells are a preferred host for expressing nucleotide segments encoding immunoglobulins or fragments thereof. See Winnacker, From Genes to Clones, (VCH Publishers, NY, 1987), which is incorporated herein by reference in its entirety. A number of suitable host cell lines capable of secreting intact heterologous proteins have been developed in the art, and include CHO cell lines, various COS cell lines, HeLa cells, L cells and multiple myeloma cell lines. Expression vectors for these cells can include expression control sequences, such as an origin of replication, a promoter, an enhancer (Queen et al., "Cell-type Specific Regulation of a Kappa Immunoglobulin Gene by Promoter and Enhancer Elements," *Immunol Rev* 89:49 (1986), incorporated herein by reference in its entirety), and necessary processing information sites, such as ribosome binding sites, RNA splice sites, polyadenylation sites, and transcriptional terminator sequences. Preferred expression control sequences are promoters substantially similar to a region of the endogenous genes, cytomegalovirus, SV40, adenovirus, bovine papillomavirus, and the like. See Co et al., "Chimeric and Humanized Antibodies with Specificity for the CD33 Antigen,"*J Immunol* 148:1149 (1992), which is incorporated by reference herein in its entirety. Alternatively, antibody coding sequences can be incorporated in transgenes for introduction into the genome of a transgenic animal and subsequent expression in the milk of the transgenic animal (e.g., according to methods described in U.S. Pat. Nos. 5,741,957, 5,304,489, 5,849,992, all incorporated by reference herein in their entireties). Suitable transgenes include coding sequences for light and/or heavy chains in operable linkage with a promoter and enhancer from a mammary gland specific gene, such as casein or beta lactoglobulin. The vectors containing the DNA segments of interest can be transferred into the host cell by well-known methods, depending on the type of cellular host. For example, calcium chloride transfection is commonly utilized for prokaryotic cells, whereas calcium phosphate treatment, electroporation, lipofection, biolistics or viral-based transfection can be used for other cellular hosts. Other methods used to transform mammalian cells include the use of polybrene, protoplast fusion, liposomes, electroporation, and microinjection (see generally, Sambrook et al., supra, which is herein incorporated by reference in is entirety). For production of transgenic animals, transgenes can be microinjected into fertilized oocytes, or can be incorporated into the genome of embryonic stem cells, and the nuclei of such cells transferred into enucleated oocytes. Once expressed, antibodies can be purified according to standard procedures of the art, including HPLC purification, column chromatography, gel electrophoresis and the like (see generally, Scopes, Protein Purification (Springer-Verlag, N.Y., 1982), which is incorporated herein by reference in its entirety).

Once expressed, the whole antibodies, their dimers, individual light and heavy chains, or other immunoglobulin forms of the present invention can be recovered and purified by known techniques, e.g., immunoabsorption or immunoaffinity chromatography, chromatographic methods such as HPLC (high performance liquid chromatography), ammonium sulfate precipitation, gel electrophoresis, or any combination of these. See generally, Scopes, PROTEIN PURIF. (Springer-Verlag, N.Y., 1982). Substantially pure immunoglobulins of at least about 90% to 95% homogeneity are advantageous, as are those with 98% to 99% or more homogeneity, particularly for pharmaceutical uses. Once purified, partially or to homogeneity as desired, a humanized or composite human antibody can then be used therapeutically or in developing and performing assay procedures, immunofluorescent stainings, and the like. See generally, Vols. I & II Immunol. Meth. (Lefkovits & Pernis, eds., Acad. Press, NY, 1979 and 1981).

Additionally, and as described herein, a recombinant humanized antibody can be further optimized to decrease potential immunogenicity, while maintaining functional activity, for therapy in humans. In this regard, functional activity means a polypeptide capable of displaying one or more known functional activities associated with a recombinant antibody or antibody reagent thereof as described herein. Such functional activities include, e.g. the ability to bind to a target antigen.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

The term "agent" refers generally to any entity which is normally not present or not present at the levels being administered to a cell, tissue or subject. An agent can be selected from a group including but not limited to: polynucleotides; polypeptides; small molecules; and antibodies or antigen-binding fragments thereof. A polynucleotide can be RNA or DNA, and can be single or double stranded, and can be selected from a group including, for example, nucleic acids and nucleic acid analogues that encode a polypeptide. A polypeptide can be, but is not limited to, a naturally-occurring polypeptide, a mutated polypeptide or a fragment thereof that retains the function of interest. Further examples of agents include, but are not limited to a nucleic acid aptamer, peptide-nucleic acid (PNA), locked nucleic acid (LNA), small organic or inorganic molecules; saccharide; oligosaccharides; polysaccharides; biological macromolecules, peptidomimetics; nucleic acid analogs and derivatives; extracts made from biological materials such as bacteria, plants, fungi, or mammalian cells or tissues and naturally occurring or synthetic compositions. An agent can be applied to the media, where it contacts the cell and induces its effects. Alternatively, an agent can be intracellular as a result of introduction of a nucleic acid sequence encoding the agent into the cell and its transcription resulting in the production of the nucleic acid and/or protein environmental stimuli within the cell. In some embodiments, the agent is any chemical, entity or moiety, including without limitation synthetic and naturally-occurring non-proteinaceous entities. In certain embodiments the agent is a small molecule having a chemical moiety selected, for example, from unsubstituted or substituted alkyl, aromatic, or heterocyclyl moieties including macrolides, leptomycins and related natural products or analogues thereof. Agents can be known to have a desired activity and/or property, or can be selected from a library of diverse compounds. As used herein, the term "small molecule" can refer to compounds that are "natural product-like," however, the term "small molecule" is not limited to "natural product-like" compounds. Rather, a small molecule is typically characterized in that it contains several carbon—carbon bonds, and has a molecular weight more than about 50, but less than about 5000 Daltons (5 kD). Preferably the small molecule has a molecular weight of less than 3 kD, still more preferably less than 2 kD, and most preferably less than 1 kD. In some cases it is preferred that a small molecule have a molecular mass equal to or less than 700 Daltons.

As used herein, the term "inhibitor" refers to an agent which can decrease the level and/or activity of a target product (e.g. antibodies with a particular antibody glycosylation state), e.g. by at least 10% or more, e.g. by 10% or more, 50% or more, 70% or more, 80% or more, 90% or more, 95% or more, or 98% or more.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. tuberculosis. The term "treating" includes reducing or alleviating at least one adverse effect or symptom of a condition, disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The term "statistically significant" or "significantly" refers to statistical significance and generally means a two standard deviation (2 SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-610: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (4 ed.), Cold Spring Harbor Laboratory Press, Cold Spring Harbor, N.Y., USA (2012); Davis et al., Basic Methods in Molecular Biology, Elsevier Science Publishing, Inc., New York, USA (1995); or Methods in Enzymology: Guide to Molecular Cloning Techniques Vol. 152, S. L. Berger and A. R. Kimmel Eds., Academic Press Inc., San Diego, USA (1987); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

All patents and other publications; including literature references, issued patents, published patent applications, and patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A method of treating a disease or condition in a subject, the method comprising:
   assaying a sample obtained from the subject determine the presence or absence of an antibody glycosylation state indicative of the disease or condition; and
   administering a treatment for the disease or condition if the antibody glycosylation state is indicative of the presence of the disease or condition.
2. The method of paragraph 1, wherein the disease is an infection.
3. The method of paragraph 2, wherein the disease is elderly flu, syphilis, legionella, lyme disease and/or CMV reactivation.
4. The method of any of paragraphs 1-3, wherein the antibody glycosylation state indicative of the disease comprises less glycosylation relative to levels found in a normal individual.

5. The method of any of paragraphs 1-4, wherein the antibody glycosylation state comprises less galactosylation, sialation, and/or fucosylation relative to levels found in a normal individual.
6. The method of any of paragraphs 1-5, wherein the antibody glycosylation state is marked by one or more different glycan structures relative to a normal individual attached to an antibody Fc-domains.
7. The method of any of paragraphs 1-6, wherein the antibody glycosylation state is marked by one or more different glycan structures relative to a latent infected patient attached to an antibody Fc-domain.
8. The method of any of paragraphs 1-7, wherein the antibody glycosylation state indicative of the disease is a decreased presence of afucosylated branched glycoforms on bulk IgG.
9. The method of any of paragraphs 1-8, wherein the antibody glycosylation state indicative of the disease comprises an inflamed antibody Fc-domain.
10. The method of any of paragraphs 1-9, wherein the antibody is an IgG antibody.
11. The method of paragraph 10, wherein the antibody is an IgG antibody from the plasma of the subject.
12. The method of any of paragraphs 1-11, wherein the antibody is antigen specific to the disease.
13. The method of any of paragraphs 1-12, wherein the treatment comprises a therapeutically effective dosage of antibody with a normal level of glycosylation relative to a healthy individual.
14. The method of any of paragraphs 1-13, wherein the disease is tuberculosis (TB).
15. The method of paragraph 14, wherein the tuberculosis is active TB.
16. The method of any of paragraphs 14-15, wherein the glycosylation state indicative of tuberculosis is selected from the group consisting of:
  decreased 2-galactose (G2): decreased fucosylated G2 (G2F); decreased fucosylated G2 with bisecting N-acetylglucosamine (G2FB); and decreased 2-galactose (G2), fucosylated G2 (G2F), and fucosylated G2 with bisecting N-acetylglucosamine (G2FB).
17. The method of any of paragraphs 1-13, wherein the condition is transplant rejection.
18. The method of paragraph 17, wherein the glycosylation state indicative of transplant rejection is selected from the group consisting of:
  increased G0FB; increased G0F; and increased G0F and G0FB but not increased G0B.
19. The method of any of paragraphs 1-13, wherein the condition is flu non-responsiveness.
20. The method of paragraph 19, wherein the glycosylation state indicative of flu non-responsiveness is selected from the group consisting of:
  increased G1; increased G0B; decreased G0F; and increased G1 and G0B but not increased G0F.
21. The method of any of paragraphs 19-20, wherein the treatment of flu non-responsiveness comprises decreasing the level and/or activity of G1 and/or G0B antibodies in the subject.
22. A method of diagnosing a disease in a subject, comprising:
  assaying a sample obtained from the subject to determine the presence or absence of an antibody glycosylation state indicative of the disease;
  diagnosing the disease in the subject based upon the presence of an antibody glycosylation state indicative of the disease.

23. A method of diagnosing susceptibility for a disease in a subject, comprising:
  assaying a sample obtained from the subject to determine the presence or absence of an antibody glycosylation state indicative of susceptibility for the disease; and
  diagnosing susceptibility for the disease in the subject based upon the presence of an antibody glycosylation state indicative of the disease.
24. The method of any of paragraphs 22-23, wherein the disease is an infection.
25. The method of paragraph 24, wherein the disease is elderly flu, syphilis, legionella, lyme disease and/or CMV reactivation.
26. The method of any of paragraphs 22-25, wherein the antibody glycosylation state indicative of the disease comprises less glycosylation relative to levels found in a normal individual.
27. The method of any of paragraphs 22-26, wherein the antibody glycosylation state comprises less galactosylation, sialation, and/or fucosylation relative to levels found in a normal individual.
28. The method of any of paragraphs 22-27, wherein the antibody glycosylation state is marked by one or more different glycan structures relative to a normal individual attached to an antibody Fc-domains.
29. The method of any of paragraphs 22-28, wherein the antibody glycosylation state is marked by one or more different glycan structures relative to a latent infected patient attached to an antibody Fc-domain.
30. The method of any of paragraphs 22-29, wherein the antibody glycosylation state indicative of the disease is a decreased presence of afucosylated branched glycoforms on bulk IgG.
31. The method of any of paragraphs 22-30, wherein the antibody glycosylation state indicative of the disease comprises an inflamed antibody Fc-domain.
32. The method of any of paragraphs 22-31, wherein the antibody is an IgG antibody.
33. The method of paragraph 32, wherein the antibody is an IgG antibody from the plasma of the subject.
34. The method of any of paragraphs 22-33, wherein the antibody is antigen specific to the disease.
35. The method of any of paragraphs 22-34, wherein the disease is tuberculosis (TB).
36. The method of paragraph 35, wherein the tuberculosis is active TB.
37. The method of any of paragraphs 35-36, wherein the glycosylation state indicative of tuberculosis is selected from the group consisting of:
  decreased 2-galactose (G2): decreased fucosylated G2 (G2F); decreased fucosylated G2 with bisecting N-acetylglucosamine (G2FB); and decreased 2-galactose (G2), fucosylated G2 (G2F), and fucosylated G2 with bisecting N-acetylglucosamine (G2FB).
38. The method of any of paragraphs 22-34, wherein the condition is transplant rejection.
39. The method of paragraph 38, wherein the glycosylation state indicative of transplant rejection is selected from the group consisting of:
  increased G0FB; increased G0F; and increased G0F and G0FB but not increased G0B.
40. The method of any of paragraphs 22-34, wherein the condition is flu non-responsiveness.
41. The method of paragraph 40, wherein the glycosylation state indicative of flu non-responsiveness is selected from the group consisting of:

increased G1; increased G0B; decreased G0F; and increased G1 and G0B but not increased G0F.

42. A method of prognosing a disease of condition in a subject, comprising:
    assaying a sample obtained from the subject to determine the presence or absence of an antibody glycosylation state which varies by a statistically significant amount relative to levels found in a healthy individual; and
    prognosing an aggressive form of the disease or condition based on the presence of an antibody glycosylation state which varies by a statistically significant amount relative to levels found in a healthy individual.
43. The method of paragraph 42, wherein the disease is elderly flu, syphilis, legionella, lyme disease and/or CMV reactivation.
44. The method of any of paragraphs 42-43, wherein the antibody glycosylation state comprises less glycosylation relative to levels found in a normal individual.
45. The method of any of paragraphs 42-44, wherein the antibody glycosylation state comprises less galactosylation, sialation, and/or fucosylation relative to levels found in a normal individual.
46. The method of any of paragraphs 42-45, wherein the antibody glycosylation state is marked by one or more different glycan structures relative to a normal individual attached to an antibody Fc-domains.
47. The method of any of paragraphs 42-46, wherein the antibody glycosylation state is marked by one or more different glycan structures relative to a latent infected patient attached to an antibody Fc-domain.
48. The method of any of paragraphs 42-47, wherein the antibody glycosylation state is a decreased presence of afucosylated branched glycoforms on bulk IgG.
49. The method of any of paragraphs 42-48, wherein the antibody is an IgG antibody.
50. The method of paragraph 49, wherein the antibody is an IgG antibody from the plasma of the subject.
51. The method of any of paragraphs 42-50, wherein the antibody is antigen specific to the disease.
52. The method of any of paragraphs 42-51, wherein the disease is tuberculosis (TB).
53. The method of paragraph 52, wherein the aggressive form of the disease is active TB.
54. The method of any of paragraphs 52-53, wherein the glycosylation state indicative of tuberculosis is selected from the group consisting of:
    decreased 2-galactose (G2): decreased fucosylated G2 (G2F); decreased fucosylated G2 with bisecting N-acetylglucosamine (G2FB); and decreased 2-galactose (G2), fucosylated G2 (G2F), and fucosylated G2 with bisecting N-acetylglucosamine (G2FB).
55. The method of any of paragraphs 42-51, wherein the condition is transplant rejection
56. The method of paragraph 55, wherein the glycosylation state indicative of transplant rejection is selected from the group consisting of:
    increased G0FB; increased G0F; and increased G0F and G0FB but not increased G0B.
57. The method of any of paragraphs 42-51, wherein the condition is flu non-responsiveness.
58. The method of paragraph 57, wherein the glycosylation state indicative of flu non-responsiveness is selected from the group consisting of:
    increased G1; increased G0B; decreased G0F; and increased G1 and G0B but not increased G0F.
59. A method of detecting infection in a subject, comprising:
    isolating pathogen specific IgG antibody from a biological sample and/or tissue obtained from the subject;
    profiling variable glycan decoration on the Fc region of the pathogen specific antibody; and detecting an active infection based on the presence of an altered glycan display on the Fc region of the pathogen specific antibody relative to an individual with latent pathogenic infection.
60. The method of paragraph 59, wherein the subject does not have signs and/or symptoms of said pathogenic infection.
61. The method of any of paragraphs 59-60, wherein infection is detected at point-of-care.
62. The method of any of paragraphs 59-61, wherein the infection is elderly flu, syphilis, legionella, lyme disease and/or CMV reactivation.
63. The method of any of paragraphs 59-62, wherein the antibody glycosylation state comprises less glycosylation relative to levels found in a normal individual.
64. The method of any of paragraphs 59-63, wherein the antibody glycosylation state comprises less galactosylation, sialation, and/or fucosylation relative to levels found in a normal individual.
65. The method of any of paragraphs 59-64, wherein the antibody glycosylation state is marked by one or more different glycan structures relative to a normal individual attached to an antibody Fc-domains.
66. The method of any of paragraphs 59-65, wherein the antibody glycosylation state is marked by one or more different glycan structures relative to a latent infected patient attached to an antibody Fc-domain.
67. The method of any of paragraphs 59-66, wherein the antibody glycosylation state is a decreased presence of afucosylated branched glycoforms on bulk IgG.
68. The method of any of paragraphs 59-67, wherein the antibody is an IgG antibody.
69. The method of paragraph 68, wherein the antibody is an IgG antibody from the plasma of the subject.
70. The method of any of paragraphs 59-69, wherein the antibody is antigen specific to the disease.
71. The method of any of paragraphs 59-70, wherein the infection is tuberculosis (TB).
72. The method of paragraph 71, wherein the glycosylation state indicative of tuberculosis is selected from the group consisting of:
    decreased 2-galactose (G2): decreased fucosylated G2 (G2F); decreased fucosylated G2 with bisecting N-acetylglucosamine (G2FB); and decreased 2-galactose (G2), fucosylated G2 (G2F), and fucosylated G2 with bisecting N-acetylglucosamine (G2FB).
73. The method of any of paragraphs 59-70, wherein the infection is flu in a non-responsive subject.
74. The method of paragraph 73, wherein the glycosylation state indicative of flu non-responsiveness is selected from the group consisting of:
    increased G1; increased G0B; decreased G0F; and increased G1 and G0B but not increased G0F.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

In one embodiment, the present invention provides for a diagnostic test for tuberculosis (TB) specifically at the primary care level. Even with recent advances in molecular diagnostics for TB, currently available methodology does not reliably diagnose *Mycobacterium tuberculosis* (Mtb) at the point of care.

Even in resource-rich settings in the United States, the initial screening test for active TB remains sputum smear microscopy. Yet, smear microscopy has changed little in more than a century, is accurate only in advanced disease with more than 10,000 mycobacteria per mL of sputum, and is often unreliable in the setting of HIV, where sputum contains many fewer Mtb bacilli. In advanced laboratories, smear microscopy is supplemented by bacterial culture, which is much more sensitive. In culture-based diagnosis, as few as 100 mycobacteria per mL of sputum can be identified, making it the most sensitive available diagnostic, even in the presence of HIV co-infection. However, because Mtb replicates so slowly, culture can take 3-8 weeks to make a diagnosis. In some places, smear and culture are further supplemented by molecular tests, which amplify and detect Mtb genetic material. PCR-based assays are highly sensitive, provide drug susceptibility information, and can be faster than culture, but are expensive, and require a laboratory capable of molecular diagnostics. Recently, a fully automated, PCR-based assay, the Xpert MTB/Rif test, has been developed. This test is able to diagnose TB directly from sputum samples in 2 hours with 73% sensitivity and can also accurately detect resistance to rifampicin. The test, however, is expensive and it requires certain infrastructure, such as a constant supply of electricity. It is therefore only amenable to the highest levels of the health system, and will not fulfill the need for a POC test.

Thus, there remains a pressing need for a rapid and sensitive TB diagnostic assay that can be used at the point-of-care. In one embodiment, the present invention provides a point of care diagnostic for tuberculosis as a fingerstick assay that distinguishes patients with active tuberculosis disease from those with latent tuberculosis infection or no infection at all. In another embodiment, antibodies in patients' serum that are diagnostic of active infection are identified. Patients with active and latent disease both harbor antibodies that recognize Mtb, but currently in the art there has been an inability to effectively distinguish the antibodies from patients with active and latent disease. However, in accordance with various embodiments herein, the inventors have developed a means by which patient subpopulations may be identified using biophysical profiling of TB-specific antibodies. In one embodiment, the diagnostic is based on the inflammatory state of the Fc-domain of the antibody, which is actively modulated during active infection. The principle behind the resolving power of this technology lies in 2 key features:
1. All TB infected/vaccinated individuals will induce TB-specific antibodies that can be captured.
2. Active TB infected patients will have inflamed antibody Fc-domains, marked by different glycan structures attached to their Fc-domains, as they have been recently exposed to the infection, compared to latent TB infected patients that have a resting immune response.

Thus, in one embodiment, the present invention provides a diagnostic test that captures TB specific antibodies, and defines active vs latent infected patient based on the glycosylation state of the antibody.

In one embodiment, the present invention provides a diagnostic that captures information related to the inflammatory status of pathogen specific antibodies by characterizing the glycosylation status of TB-specific antibodies from infected patients. In another embodiment, the specific features that are defined is the level of galactosylation/fucosylation/sialation of the antibody, as less galactosylated/sialated/fucosylated antibodies are considered to be more inflammatory. The degree of glycosylation may therefore represent a measure of the activity of the infection.

In one embodiment, the diagnostic may incorporate an ELISA type diagnostic assay. In another embodiment, the invention may include clinical management of many other infections (elderly flu, syphilis, legionella, lyme disease, CMV reactivation, etc) which would also benefit from a diagnostic that examines the inflammatory state of the antibody. This measure of immune modulation of the B cell response could provide important data related to the functionality of the antibody (flu) and/or the disease state of the infected individual.

The importance of host humoral immunity in tuberculosis (TB) disease is unclear. It is demonstrated herein that IgG from patients infected with latent TB are capable of inducing stronger antibody dependent cellular cytotoxicity (ADCC) and NK cell mediated Fc effector functions compared to active TB. Furthermore, modulation of the distinct Fc-functional responses coincided with different biophysical characteristics were distinctly different between patients with latent and active infections, including differences and glycoforms observed on both bulk and PPD-specific IgG. Interestingly, glycan analysis also indicates a less inflammatory state during latent disease while functionality appears to be higher. Finally, it is demonstrated that IgG from patients infected with latent but not active TB are capable of inducing mycobacterial killing in human macrophages in a single cell imaging assay. Together, these data highlight the importance of the changing immune balance during TB disease progression through antibody function and argue that Fc-glycosylation structures can serve as immune correlates for more effective diagnostic and therapeutic interventions.

Tuberculosis (TB) is one of the world's deadliest diseases, with over 9 million new cases of infection and 1.7 million fatalities annually arising from the bacterium, *Mycobacterium tuberculosis* (Mtb) (1). Despite centuries of research, current T cell based diagnostics and therapeutics are poor modalities of management. The Mantoux test with purified protein derivative (PPD) and the IFN-□ELISA assays remain with a wide range of sensitivity and specificity (from 58% to 100%) based on operator and technical details and populations (2). Similarly the only licensed TB vaccine currently in use, Bacille Calmette-Guérin (BCG), has variable efficacy averaging approximately 50%(3) with most protection seen in children from TB meningitis, but less in adult pulmonary TB which represents the overwhelming proportion of cases (4). Thus new efficacious vaccine strategy approaches and improved diagnostic capabilities are urgently needed.

Approximately 90% of adults infected with Mtb never develop symptoms of clinical disease, resulting in latent TB infections (LTBI). This is compelling evidence that the immune system is capable of mounting a protective response. Although many biomarkers have been proposed and T cell mediated immunity is clearly important, the critical immune features are unclear (5, 6). Recently, it has been shown that even within a single host, individual granulomas containing Mtb behave heterogeneously through differential killing of the organism (7). The mechanism that drives this variability remains to be elucidated but many of the lesions contain antibody (Ab) producing plasma cells. (8, 9) Moreover, B cells and Ab-antigen complexes have been implicated in granuloma development and Mtb immunity. In humans, Mtb-specific Abs appear to confer protection against disseminated TB disease (10, 11), promote Mtb killing by innate cells and enhance stimulation of Mtb-specific CD4 and CD8 T cell responses (12). Indeed, previous studies have demonstrated a protective role for antibodies using passive immunization (13, 14). More specifically, mice lacking the activating Fc gamma chain receptor are more susceptible to infection and advanced pulmonary disease compared to wildtype, while those lacking the inhibitory receptor have improved pulmonary control of their disease (15). Therefore, strong support exists for the role of antibodies in protecting against Mtb though the mechanism remains elusive.

Antibodies are capable of providing immune protection through multiple mechanisms (16). Innate immune recruitment of antibodies is important in natural killer (NK) cell-mediated Ab dependent cellular cytotoxicity (ADCC) of bacteria such as Cryptococcus neoformans (17) and monocyte and macrophage mediated Ab dependent cellular phagocytosis (ADCP) of bacteria including *Salmonella enterica* (18) and Borrelia burgdorferi (19). Moreover, the fact that several bacteria have evolved to encode enzymes that specifically protect them from the innate immune recruiting properties of Abs (20, 21), further supports the notion that these non-neutralizing anti-microbial properties of Abs play a vital role in protection from bacterial infection. However, little is known about these types of humoral immune responses in the context of Mtb infection.

It is demonstrated herein that PPD-specific IgG IgG from patients infected with latent (LTBI) but not active TB are capable of mediating distinct Fc-effector responses. Sera from patients with LTBI have more ADCC compared to those with TBI. Modulation of the different Fc-mediate effector responses was correlated with, FcR affinity, IgG subclass and alterations of Fc glycosylation structures. Intriguingly a less inflammatory Fc glycosylation state during LTBI appears to correlate with improved ADCC function. Of interest, IgG from patients infected with LTBI but not active TB were capable of inducing mycobacterial killing in human macrophages in a novel single cell imaging assay Together, these data highlight the importance of the changing immune balance during TB disease progression through antibody function and argue that Fc-glycosylation structures can serve as immune correlates for more effective diagnostic and therapeutic interventions.

LTBI and TB Samples

Study population and sample collection. Twelve subjects with latent *M. tuberculosis* infection (LTBI) and twelve with active pulmonary tuberculosis (TB) disease were recruited for this study from the Cape Town region of South Africa. All subjects were ≥18 years of age. LTBI was defined by the presence of IFN-γ-producing T cells specific for CFP-10 and/or ESAT-6 peptides in a short-term whole blood intracellular cytokine staining (ICS) assay, with no previous history of TB diagnosis or treatment. All TB patients had either positive sputum smear microscopy and/or positive culture for *M. tuberculosis*. Peripheral blood was obtained in sodium heparin Vacutainer tubes (BD Biosciences), and plasma was isolated by centrifugation within 4 hours of collection. Blood from individuals with TB was obtained prior to or within 7 days of starting standard course anti-TB treatment, which was provided according to South African national health guidelines. All study participants gave written, informed consent for the study, which was approved by the Human Research Ethics Committee of the University of Cape Town, the Western Cape Department of Health, and the Massachusetts General Hospital.

Bulk IgG Purification

IgG was purified from plasma of LTBI and TBI using Melon Gel columns according to the manufacturer's instructions (Thermo Scientific). Total IgG concentration was calculated by Human IgG ELISA kit (MABTECH).

TB Specific-Binding Titers

ELISA plates (Nunc) were coated overnight at 4° C. with 80 µl of PBS containing 250 ng/ml PPD per well; identical plates were blocked with 100 µl of PBS-A (PBS containing 5% BSA) per well and used as sample background controls. The wells were washed six times with PBS-T (PBS containing 0.05% Tween 20), blocked with 100 µl of PBS-A per well for 2 hrs, and washed again. Serial dilutions of purified IgG, starting at 1 mg/ml, were then added to each well (81 µl) in replicate, and the plates were incubated at room temperature for 2 hrs. After six washes with PBST, 100 µl/well of a horseradish peroxidase-conjugated anti-human IgG (diluted 1:500 in PBS; R&D Systems) was added to the wells. The plates were incubated for 1 hr at RT, washed six times, and developed via the addition of 50 µl of 0.4 mg/ml o-phenylenediamine in PBS/H2O2. The reaction was stopped by the addition of 50 µl/well of stop solution (2.5 M H2SO4), and the optical density at 492 and 605 nm was read on a Tecan ELISA reader.

THP-1 Phagocytosis Assay

The THP-1 phagocytosis assay was performed as previously described. Briefly, THP-1 cells (ATCC) were cultured as recommended. Biotinylated PPD was used to saturate the binding sites on 1 um fluorescent neutravidin beads (Invitrogen) overnight at 4° C. Excess antigen was removed by washing the pelleted beads, which were then incubated with patient Ab samples for 2 hrs at 37° C. Following opsonization, THP-1 cells were added to the bead/Ab mix and incubated overnight to allow for phagocytosis. Following this incubation, the cells were fixed, and bead uptake was measured using flow cytometry on a BD LSRII equipped with high-throughput sampler. Phagocytic scores are presented as the integrated MFI (iMFI; frequency×MFI).

RFADCC Assay

A modified rapid fluorometric ADCC (RFADCC) assay was used. In brief, the CEM-NKr CCR5+ T lymphoblast cell line was pulsed with PPD (60 µg/ml), then labeled with the intracellular dye CFSE and the membrane dye PKH26. Both PBMCs and NK cells were isolated from healthy donor whole blood with RosetteSep (Stem Cell Technologies). Purified IgG was added to the labeled CEM-NKr cells, which were then incubated with PBMC or NK cells for 4 hr at 37° C. The cells were fixed, and the proportion of PKH26+ cells that had lost intracellular CFSE staining (i.e., lysed target cells) was determined using flow cytometry.

FcγR Surface Plasmon Resonance (SPR) Analysis

For surface plasmon resonance (SPR) experiments run on a Biacore 3000 machine, research grade CMS plasmon surface resonance chips were coated with FcγRIIa, IIb, Ma or no protein (PBS). In parallel, the subject antibodies were ran at 125 ug/ml, in 96-well plates, on a Biacore 3000. The binding of antibodies to the individual FcγRs was quantified as the relative response units of signal following each sample injection.

Customized Luminex Subclass Assay

A customized Luminex subclass assay was used to quantify the relative concentration of each Ab isotype among PPD antigen-specific Abs. Briefly, carboxylated microspheres (Luminex) were coupled with PPD protein by covalent NHS-ester linkages by combining EDC and NHS (Thermo Scientific) in PBS per the manufacturer's instructions. The loaded microspheres (50 µl of 100 microspheres/µl in 0.1% BSA/PBS) were added to each well of a 96-well filter plate (Millipore). Each IgG sample (50 µl of purified bulk IgG diluted to 100 µg/ml) was added to five replicate wells of the 96-well plate and incubated overnight at 4° C. The microspheres were then washed three times with 100 µl of PBST. IgG detection reagents specific for IgG1, IgG2, IgG3, IgG4 or pan IgG conjugated with PE (Southern Biotech) were added individually to the replicate wells containing the bound Abs. The 96-well plate was incubated with shaking for 2 hr, washed three times and read on a Bio-Plex 200 System. The background signal, defined as the MFI of microspheres incubated with detection reagents in the absence of clinical Abs, was subtracted from each sample.

Glycan Profiling of Bulk IgG 20 ug of purified bulk IgG was denatured and treated with PNGase enzyme (NEB) to release N-linked glycans. Proteins were precipitated in ice-cold ethanol and the glycan containing supernatants were dried in a Centrivap. Dried glycans were fluorescently labeled with a 1:1 ratio of 50 mM APTS (8-aminoinopyrene-1,3,6-trisulfonic acid, Life Technologies) in 1.2 M citric acid and 1 M Sodium cyanoborohydride in tetrahydrofuran (Sigma-Aldrich) at 55° C. for 2 hours. Labeled glycans were dissolved in ultrapure water and excess unbound APTS was removed using Bio-Gel P-2 (Bio-rad) size exclusion columns. Samples were run with a LIZ 600 DNA ladder in Hi-Di formamide (Life Technologies) on an ABI 3130X1 DNA sequencer. Data was analyzed using GeneMapper software and peaks were assigned based on migration of known standards and glycan digests. Peak area was calculated and used to determine the relative percentage of each glycan structure.

Mtb Strains and Growth Conditions

The Mtb H37Rv transcriptional reporter strain was grown in Middlebrook 7H9 or 7H10 media supplemented with 10% OADC (Oleic Albumin Dextrose Catalase, Becton Dickinson), glycerol, and 0.05% Tween 80 with hygromycin (50 ug/ml). This strain has been described elsewhere (Martin, 2013).

Human Monocyte-Derived Macrophage (MDM) Isolation mTB negative blood donor blood was diluted with an equal volume of sterile 1×PBS and layered on top of an equal volume of Ficoll. The Ficoll gradient was centrifuged for 30 minutes at 400 rcf without brake to separate white blood cells from serum and red cells. The lymphocyte layer was recovered by pipette aspiration and washed twice with PBS at 200 rcf to remove platelets. Monocytes were recovered by positive CD14+ antibody selection (Stemcell Technologies, Tukwila, Wash.) per manufactures instructions. Monocytes remained in culture for 6 days in RPMI (Invitrogen) with human serum (Valley Biomedical, Winchester, Va.) in low-adherent conditions before infection.

ADCC Assay

Frozen stocks of Mtb was grown in 7H9 media at 37° C. for two to three days to an OD of ~0.4. Bacteria were then washed in RPMI with human serum two times. Re-suspended bacteria were then sonicated for 5 seconds, twice. Bacteria were then filtered using a 5 uM filter to obtain a single cell suspension. Bacterial number/ml was estimated from the OD600 measurement. Bacteria were added to human monocyte-derived macrophages at an MOI of 1:1. 23 hours post-infection, IgG purified from either LTBI or TBI patient sera was added to the infected cultures, and the culture was supplemented with Il-2. One hour following antibody addition, autologous NK cells were added to macrophages at an MOI of 10:1, respectively. Infection was allowed to proceed for 5 days.

Colony-Forming Units

Infected macrophages were lysed in water for 5 minutes to release intracellular bacteria. Supernatant was collected. 7H9 was added to the supernatant at 5 times the volume of water. The supernatants were stored at −80° C. until diluted and plated for Mtb colonies on 7H10 plates supplemented with hygromycin (50 ug/mL).

Statistics

All initial assays were performed blinded and only at the point of statistical analysis did unblinding take place. Univariate statistical analysis was performed using GraphPad Prism™. Mann-Whitney test was used to compare continuous outcomes between the two cohorts. For paired and more than two groups comparisons of continuous outcomes, Wilcoxon signed-rank and Kruskall-Wallis tests were used. Spearman rank correlations were used to examine bivariate associations between continuous outcomes. All p-values are two-sided and were not corrected for multiple comparisons. Multivariate classification analysis was performed by partial least squares discriminant analysis (PLSDA) using the Mathworks Statistics Toolbox for MATLAB™ (version R2014a). PLSDA is an asymmetric "discriminative" form of supervised principal component analysis (27) where the response variable indicates the class or category of the samples, in this case: LTBI or TBI, thus allowing for the supervision and classification of data to evaluate the differences between the two groups. PLS-DA was performed using all measured parameters, as well as subsets of parameters to explore how well the cohort class could be predicted using Fc function/isotype or glycan. To assess generalizability of the cohort differences within the limits of the small dataset, a leave-one-out cross-validation (LOOCV) was performed. In LOOCV, a model is trained on all but one sample and the predictive accuracy assessed for that left-out sample, this is repeated to leave out each sample and the accuracy averaged.

Higher PPD-Specific Binding Titers are Detectable in TBI Subjects

Figure 1A:
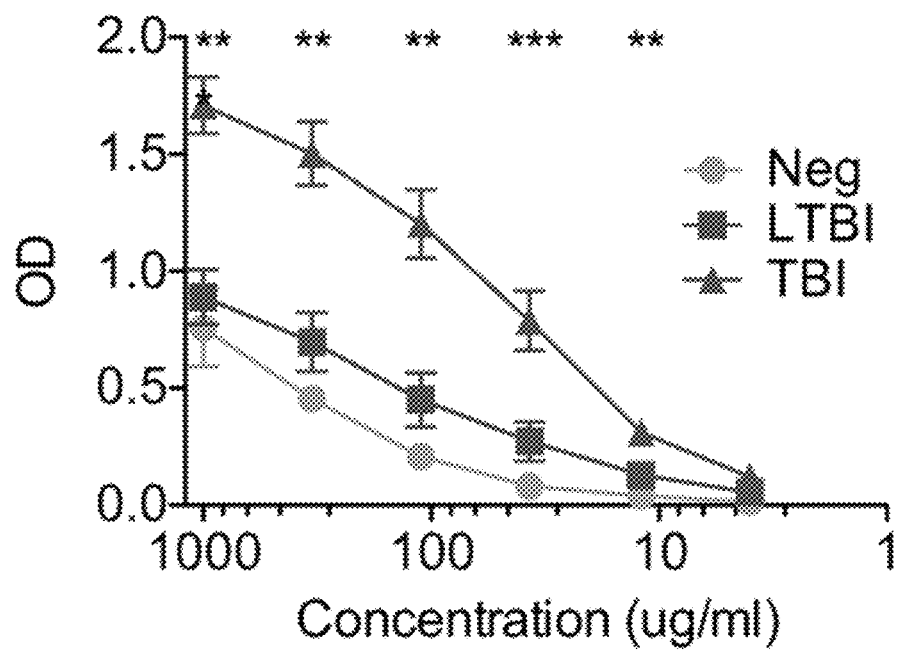
FIGS. 1A-1B demonstrate that PPD-specific IgG binding titers. LTBI and TBI plasma samples were purified for IgG using melon gel resin and was then titrated from 1000 to 1 µg/ml at 1:3 dilutions and tested for binding to PPD by ELISA (FIG. 1A).
Figure 1B:
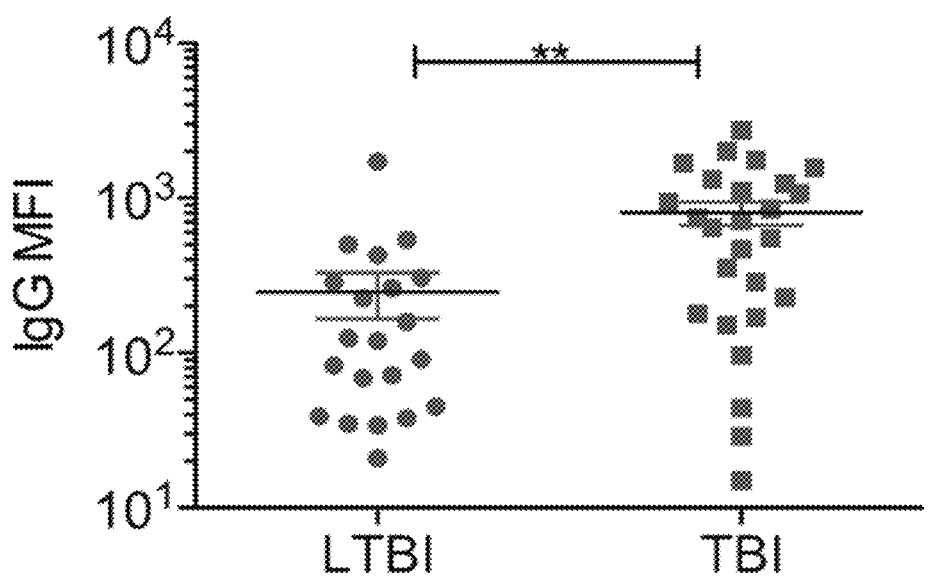

While TB-specific antibodies are commonly generated upon infection of Mtb, the role of these antibodies on TB infection remains unclear. The inventors aimed to determine if the total IgG PPD-binding titers differed between LTBI and TBI subjects, using both ELISA and luminex measurements, higher levels of PPD-specific IgG were observed in the TBI cohort compared to LTBI subjects (FIGS. 1A-1B). This result is most likely due to the higher amount of antigen exposure that occurs in TBI subjects.

Higher PPD-Specific ADCC Induced by Latent TBI Subjects

Figure 2A:
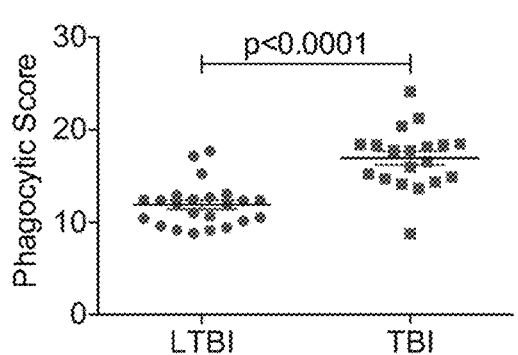
FIGS. 2A-2H demonstrate PPD-specific Fc-mediated function. All LTBI and TBI samples were assayed for (FIG. 2A) ADCP activity via a THP-1 phagocytosis assay.
Figure 2B:
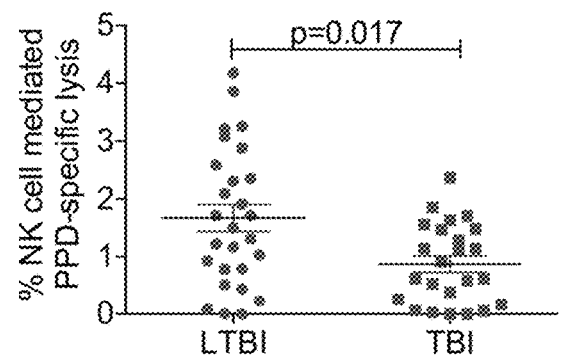
Figure 2C:
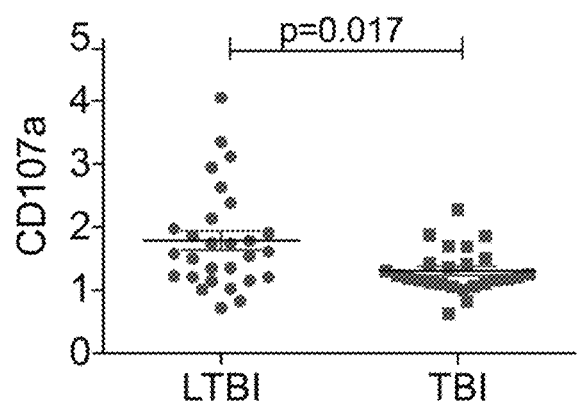
Figure 2D:
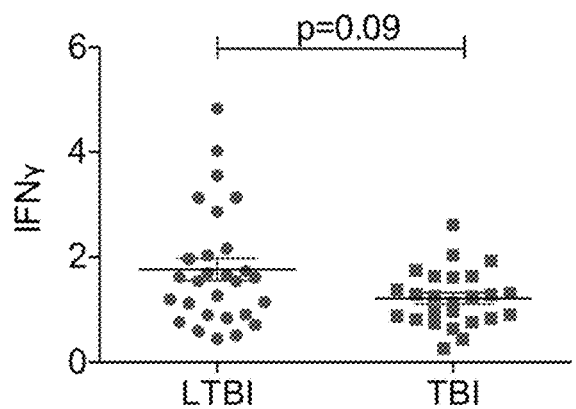

Previous studies have indicated a potential role of innate immune recruiting Ab in the control of several intracellular pathogens including malaria, viral infections and various bacteria. Thus, to comprehensively compare the innate immune effector profiles of TBI and LTBI individuals, the inventors tested the ability of antibodies to mediate both ADCP and ADCC. Antibodies from the TBI and LTBI cohorts induced ADCP uptake of PPD coated beads into macrophages, equally (FIG. 2A).

Figure 2E:
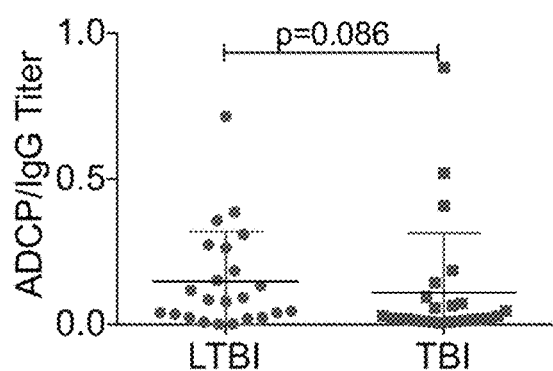
Figure 2F:
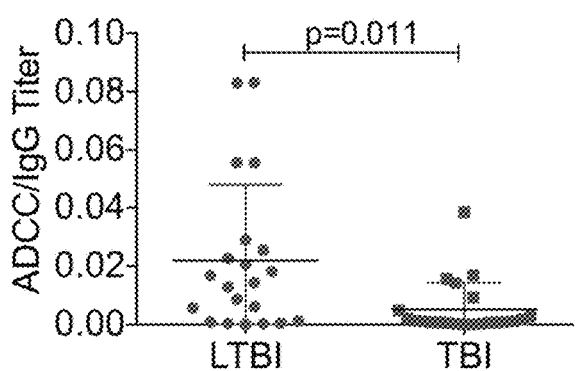
Figure 2G:
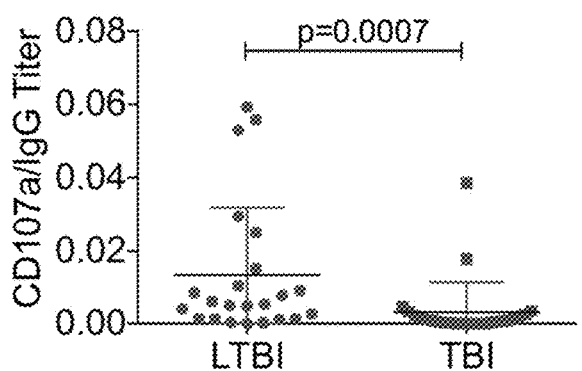
Figure 2H:
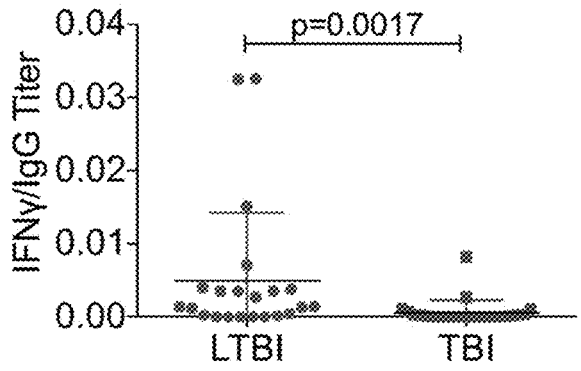

To test the ADCC activity of these antibodies, the inventors used a modified rapid fluorometric (RF)-ADCC assay that measures the ability of IgG to recruit the cytotoxic capacity of isolated NK cells. Interestingly, it was found that IgG antibodies purified from LTBI individuals mediate enhanced PPD-specific cytotoxicity as compared to IgG from active TB individuals (p=0.01, FIG. 1C). Furthermore, Abs from both cohorts were also tested for the ability to mediate CD107a degranulation and IFNγ, markers of Ab mediated NK cell cytotoxicity and activation. Similar to ADCC activity, Abs from LTBI subjects were able to induce stronger CD107a degranulation (p=0.0007, FIG. 1D) and IFNγ secretion (FIG. 2E, p=0.007) compared to active TB subjects, thus, indicating that the PPD-specific antibody Fc-effector activity appears to be higher in LTBI compared to active TB individuals.

Different FcγR Binding Affinity Profiles are Observed from LTBI and TBI Subjects As changes in Fc effector activity are driven by antibody affinity to specific Fc receptors, the inventors tested the hypothesis that the antibodies generated during active tuberculosis have a different Fc receptor affinity profile from those generated during latency. They used surface plasmon resonance (SPR) technology to quantify the binding profile of bulk purified plasma IgGs to activating Fc receptors (FcγRIIa and FcγRIIIa) and inhibitory Fc receptors (FcγRIIb). Interestingly, it was found that the Fc receptor binding differed between LTBI and TBI antibodies.

Figure 3A:
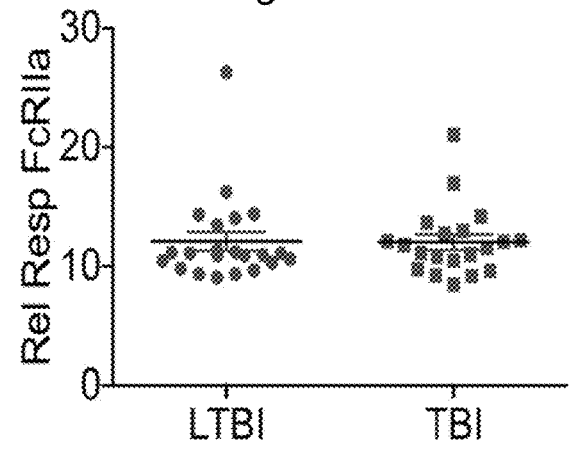
FIGS. 3A-3I demonstrate differential FcR binding affinity, especially to FcRIIIa is observed between LTBI and TB subjects and that FcRIIIa binding affinity correlates with Fc effector functions. FcR binding affinity was measured by a Plasmon Surface Resonance based system where purified IgG was passed over chips coated with different FcRs. Differences in FcR binding affinity between LTBI and TB are shown in (FIG. 3A) FcRIIa, (FIG. 3B) FcRIIb, (FIG. 3C) FcRIIIa, Ratios of the activating receptors against the inhibitory receptor FcRIIb were also determined (FIG. 3D) FcRIIa:FcRIIb and (FIG. 3E) FcRIIIa:FcRIIb. Fc-effector functions (FIG. 3F) ADCP.
Figure 3B:
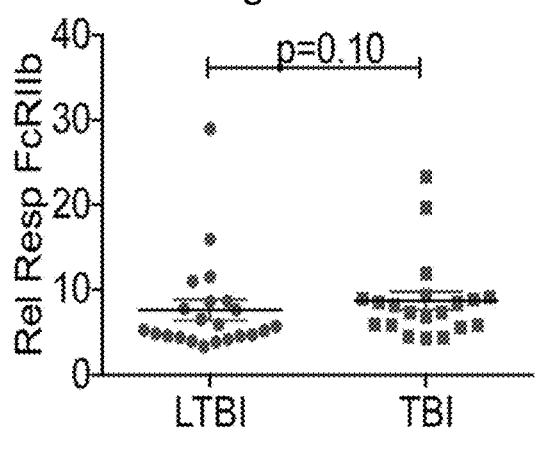
Figure 3C:
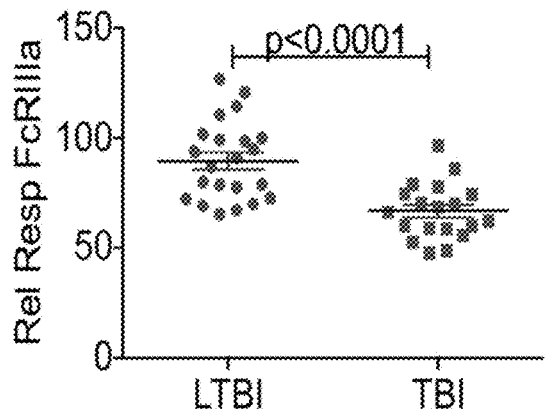
Figure 3D:
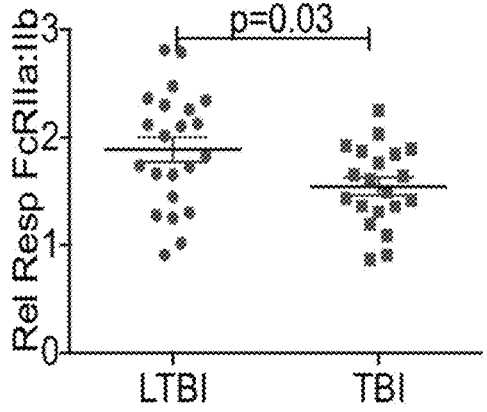
Figure 3E:
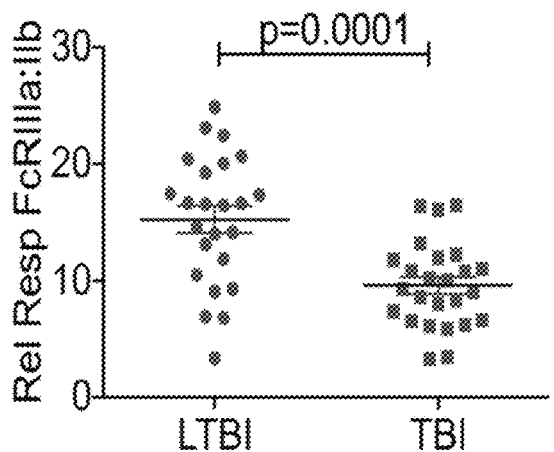
Figure 3F:
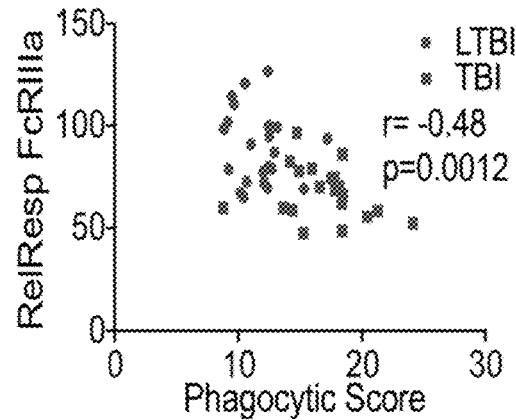

No differences were observed in binding to FcγRIIa between the two cohorts (p=0.67, FIG. 3A), IgG from LTBI had significantly higher affinity to FcγRIIIa (p<0.0001, FIG. 3C), compared to TB, the key FcγR required for ADCC and NK cell activation. While both FcγRIIa, and FcγRIIIa are activating receptors involved in mediating Fc-effector functions (30), only engagement of FcγRIIb negatively regulates phagocytes and B cells (31), potentially dampening immune activation, cytokine storm, and plasma cell survival (32). LTBI purified IgG trended towards lower affinity to inhibitory FcγRIIb (p=0.10, FIG. 3B). To estimate the inhibitory role of FcγRIIb upon innate immune effector cell recruitment the ratio of affinity between FcγRIIa:FcγRIIb and FcγRIIIa:FcγRIIb were calculated. LTBI IgG antibodies had significantly increased ratios of both FcγRIIa:FcγRIIb (p=0.03, FIG. 3D) and FcγRIIIa:FcγRIIb binding (p=0.0001, FIG. 3E) compared to TBI IgG. Therefore, preferential binding of LTBI antibodies to activating FcγRIIa and FcγRIIIa which primarily mediate Fc effector functions over inhibitory FcγRIIb engagement potentially account for the higher ADCC, NK cell activity observed on a per antibody basis.

While all FcγRIIa, and FcγRIIIa are activating receptors involved in mediating ADCP and ADCC, only engagement of FcγRIIb negatively regulates phagocytes and B cells, potentially dampening immune activation, cytokine storm, and plasma cell survival. Therefore, to estimate the inhibitory role of FcγRIIb upon innate immune effector cell recruitment the inventors also calculated the ratio of affinity between FcγRIIa:FcγRIIb and FcγRIIIa:FcγRIIb. LTBI IgG antibodies had significantly increased ratios of both FcγRIIa:FcγRIIb (p=0.03, FIG. 3D) and FcγRIIIa:FcγRIIb binding (p=0.0001, FIG. 3E) compared to TBI IgG. Therefore, preferential binding of the LTBI antibodies to activating FcγRIIa and FcγRIIIa, which primarily mediated Fc-effector functions, balanced by lower FcγRIIb engagement suggest that antibodies generated during active tuberculosis reflect a bulk IgG difference of more inflammatory activity and potentially accounting for the higher ADCC activity observed.

Figure 3G:
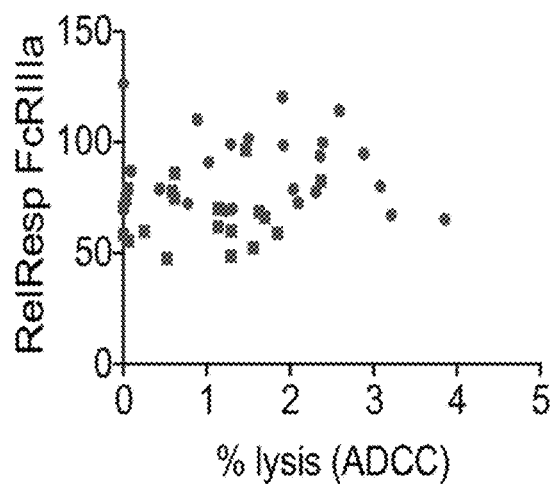

The inventors also looked for correlations between FcγR binding affinity of the TBI and LTBI antibodies with the ability to mediate ADCC and ADCP. They did not detect a significant correlation between ADCC activity and FcγR binding affinity for either of the TB antibody cohorts (FIG. 3G). In contrast, antibodies generated during TBI exhibited a strong correlation between ADCP and FcγR affinities (FIG. 3F-3J). They did not detect strong correlations between ADCP and FcγR affinities with LTBI antibodies (FIGS. 3F-3H), however, In contrast, correlations were observed between ADCP (r=−0.48, p=0.0012, FIG. 3F), CD107a (r=0.28, p=0.07, FIG. 3H) and IFNγ (r=0.40, p=0.009, FIG. 3I) with FcγRIIIa affinities. These data indicate that the differential binding of IgG to FcγRIIIa in particular may be key to the significantly distinct functional abilities in LTBI.

PPD-Specific IgG3 Levels Induced in Active TB are Associated with Enhanced ADCP and FcγR2 Binding The ability of an antibody to recruit innate immune Fc-effector activity can also be determined by its isotype and subclass. Particular subclasses can bind with higher affinity to specific Fc receptors (FcR). Thus the inventors sought to determine if the differences observed between antibodies from the two cohorts were modulated by unique PPD-specific IgG subclass profiles, testing for IgG1, IgG2, IgG3 and IgG4 isotypes. The inventors found that the abundance of different antibody IgG subclasses were similar between antibodies generated in LTBI and TBI. They next determined if a specific antibody subclass correlated with Fc-activity.

Figures 5E, 5F:
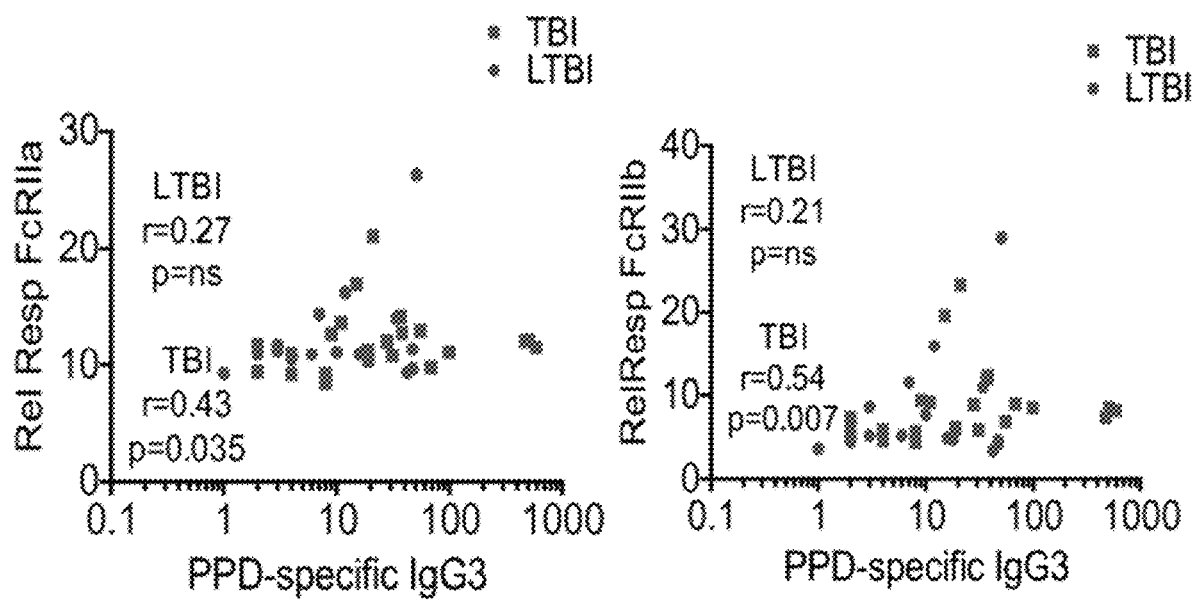
Figure 5G:
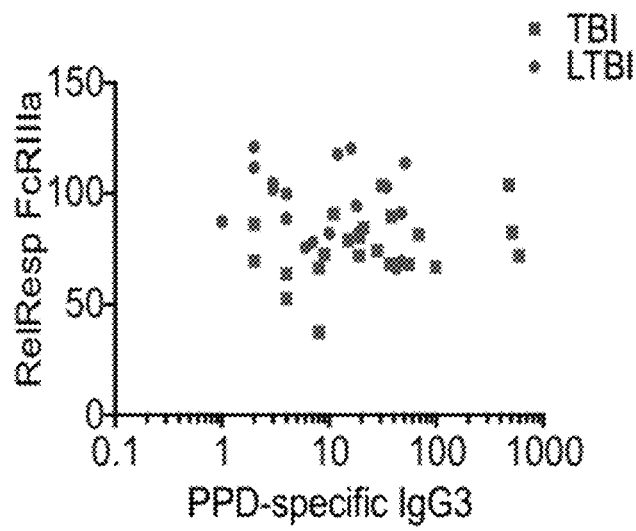

As individual antibody subclasses have the capacity to differentially induce Fc-activity through different affinities for Fc-receptors, with IgG3 exhibiting the highest affinity for all Fcγ-receptors, we next examined the relationship between PPD-specific IgG3 antibody levels and antibody functionality and affinity for distinct Fc-receptors. PPD-specific IgG3 levels were robustly associated with the induction of antibody mediated phagocytosis (FIG. 5A) in patients with active TB but not in patients with latent tuberculosis. No relationship was observed between PPD-specific IgG3 levels and ADCC in either patient population. Additionally, PPD-specific IgG3 levels in patients with active TB were significantly associated with binding to the phagocytic receptors FcγRIa (FIG. 5E) and FcγRIIb (FIG. F), but not to FcγRIIIa (FIG. 5G). In contrast, no relationship was observe between PPD-specific IgG3 levels and any Fcγ-receptor binding profiles among the latently infected Tb patients. These data suggest that changes in IgG3 levels may selectively drive alterations in antibody functionality via the recruitment of distinct Fcγ-receptors, and provide another level by which distinct antibody profiles induced during active and latent tuberculosis infection may be distinguished.

Figure 6A:
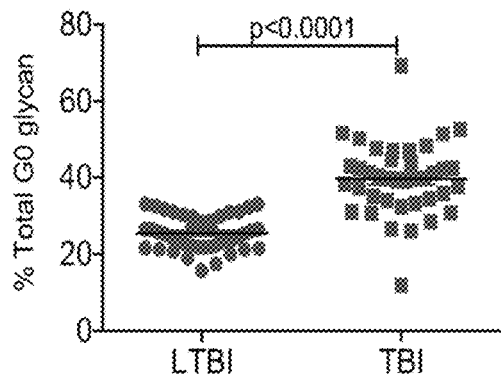
FIGS. 6A-6L demonstrate that different glycan structures are present on bulk (FIGS. 6A-6F) and PPD-specific IgG (FIGS. 6G-6L) from LTBI and TB subjects. Bulk purified IgG was denatured and treated with PNGase enzyme (NEB) to release N-linked glycans. Glycans were than sequenced and compared between LTBI and TBI subjects.
Figure 6B:
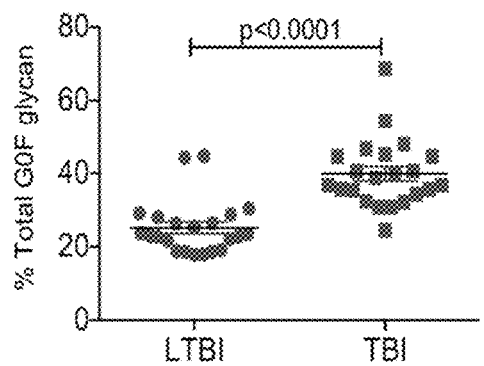
Figure 6C:
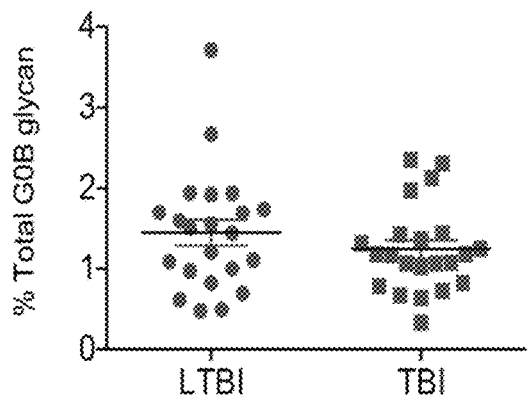
Figure 6D:
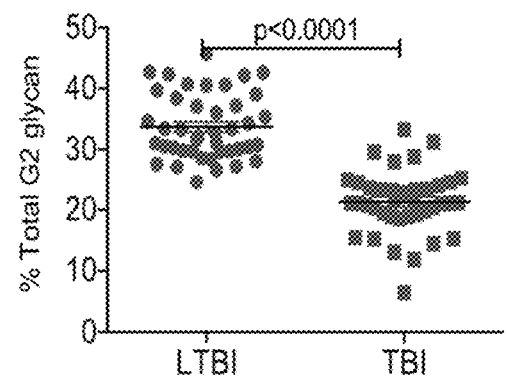
Figure 6E:
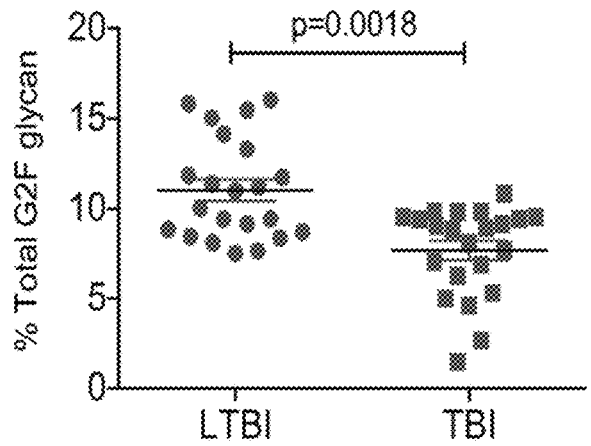
Figure 6F:
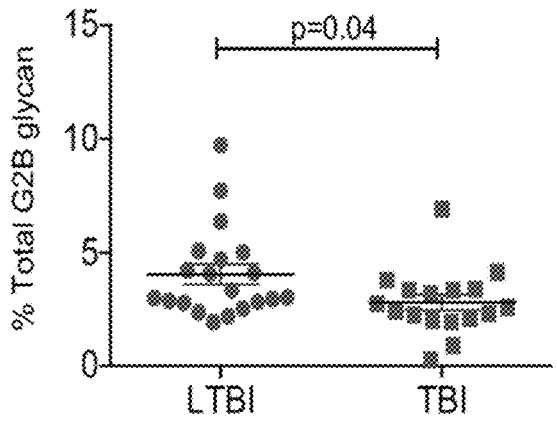
Figure 6G:
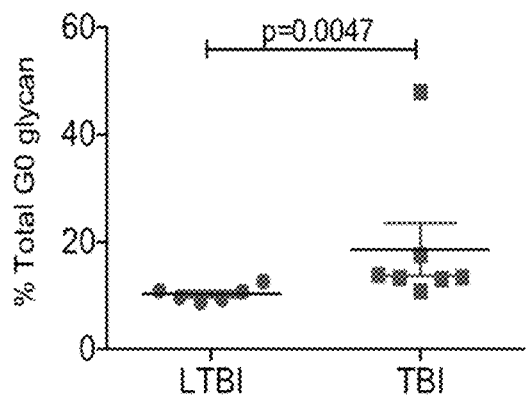
Figure 6H:
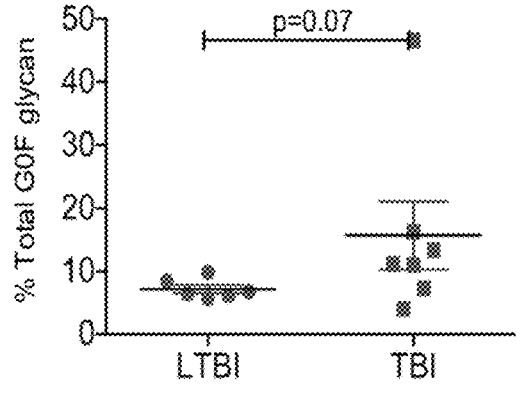
Figure 6I:
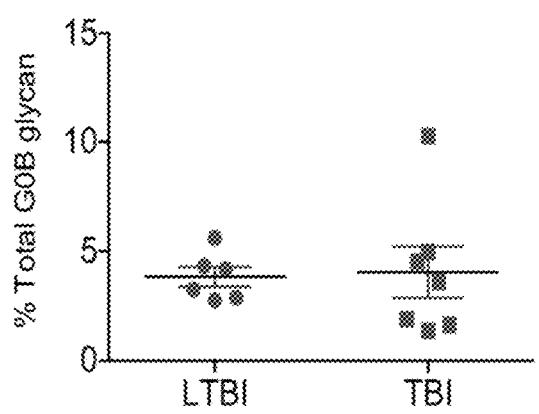
Figure 6J:
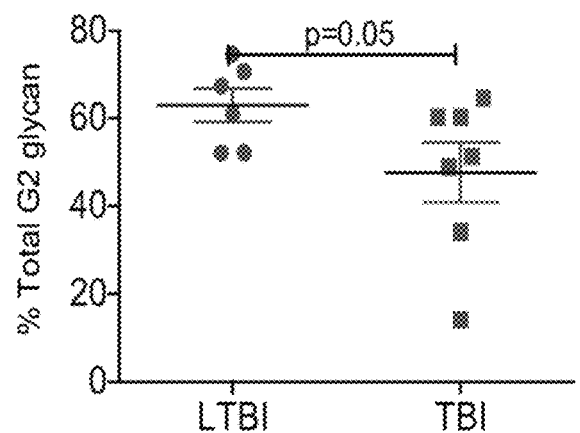
Figure 6K:
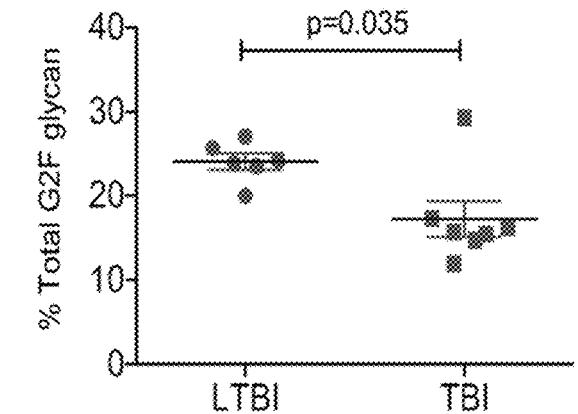
Figure 6L:
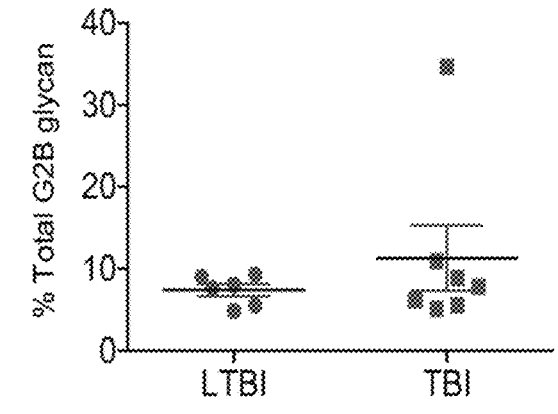

LTBI subjects have less inflammatory glycan structures. To determine if there were differences mediated by glycan binding between LTBI and TBI, purified IgG were digested to release glycan structures and the glycans sequenced, determining the bulk distribution of specific glycan structures. It was observed that purified IgG from LTBI patients were coated with significantly lower pro inflammatory glycan lacking any Galactose structures (G0) (p<0.0001, FIG. 6A) while having significantly higher anti inflammatory glycans containing 2-Galactose (G2) units (p<0.0001, FIG. 6D) when compared to active TB patients. The specific glycoforms were further resolved within the total G0 and G2 glycan population. In LTBI patients, G0F (Fucosylated G0) glycoforms were decreased compared to TBI patients (p<0.0001, FIG. 6B), while both G2F (Fucosylated G2, FIG. 6E p=0.018) and G2B (G2 with bisecting GlcNAc, FIG. 6F p=0.04) glycoforms were significantly higher, thus suggesting at a global level, IgG glycosylation is significantly altered depending on TB disease state. These differences are recapitulated in a more Mtb specific manner using PPD-specific as opposed to bulk IgG from 6 patients randomly selected from each cohort. Despite the smaller sample size, we still observed statistically significant similar IgG glycan profiles on the PPD-specific IgG, with reduced G0 (p=0.0047, FIG. 6G) and elevated G2 (p=0.05, FIG. 6J) in LTBI. Interestingly, while a trend of lower G0F (p=0.07, FIG. 6B) was observed in LTBI, G2F was higher (p=0.035, FIG. 6K). This suggests that in LTBI, the increased ADCC activity associated with the G2 state may be less dependent on afucosylation as previously described.

Antibody Glycosylation is Associated with Antibody Functionality

Figure 7A:
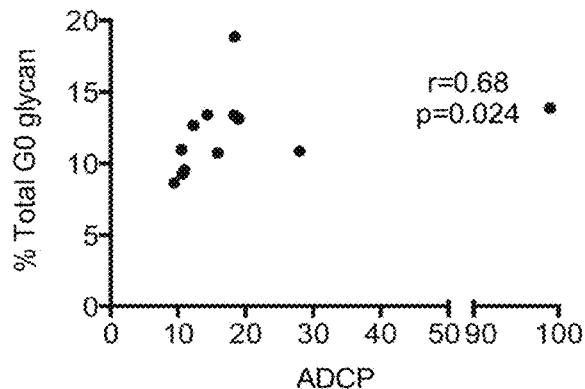
FIG. 7A-7D demonstrates that different glycan structures are associated with Fc-effector function. Total G0 glycans, from PPD specific IgG glycan isolations (FIGS. 7A-7B) as well as bulk IgG isolations (FIGS. 7C-7D), were correlated with Fc-effector function (FIG. 7A, 7C) ADCP and (FIG. 7B, 7D) ADCC.
Figure 7B:
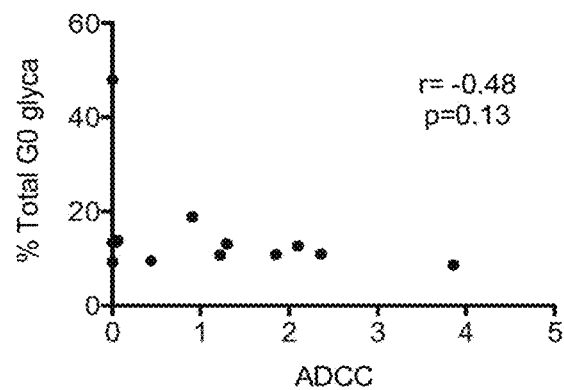
Figure 7C:
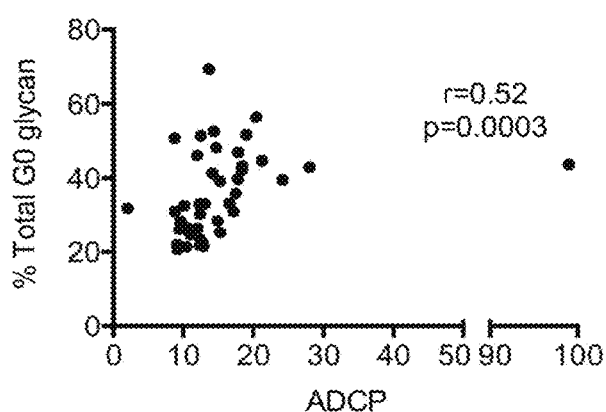
Figure 7D:
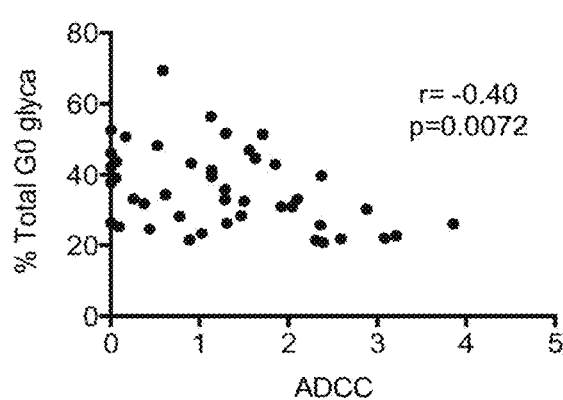

Because antibody glycosylation plays a key role in modulating antibody effector function, via altered Fcγ-receptor binding profiles, we next examined the relationship between altered Fc-glycosylation and PPD-specific antibody function. The levels of a galactosylated antibodies in both the antigen-specific (FIG. 7A) and bulk antibodies (FIG. 7C) was strongly associated with elevated phagocytosis. In contrast, changes in galactose content on antigen-specific antibodies was not associated with ADCC activity (FIG. 7B) but was inversely associated with ADCC activity in total antibody glycans (FIG. 7D) suggesting that distinct antibody glycan profiles may be induced to induce differential antibody functionality.

Multivariate analysis of Fc features clearly differentiate LTBI from TBI patients. Given the dynamic and complex interplay that the afore measured Fc features can contribute to Fc-effector responses, all the above mentioned parameters were integrated, including the Fc-functional responses (PPD-specific ADCC, ADCP, cytokine and degranulation), ability to bind to Fc-receptors and assessed glycosylation state, together, to determine multivariate differences in antibody Fc-profiles between the two cohorts through partial least squares discriminant analysis. Clear separation between the two cohorts were observed (FIGS. 8A-8C) and based on cross validation of the model's performance, these analysis strongly indicate that different mTB disease states is associated with functionally distinct antibodies. Interestingly, the most pronounced separation was observed in the multivariate analysis comparing all the glycans data (FIG. 8B) which induced the highest leave one out cross validation success (CV:91.9%) and lowest CV root mean squared error (0.62). Collectively, the analysis of Fc profiles indicates mTB disease state can be detected through, e.g., the combined assessment of distinct antibody Fc-profiles, strongly influenced by IgG glycosylation states.

Figure 9:
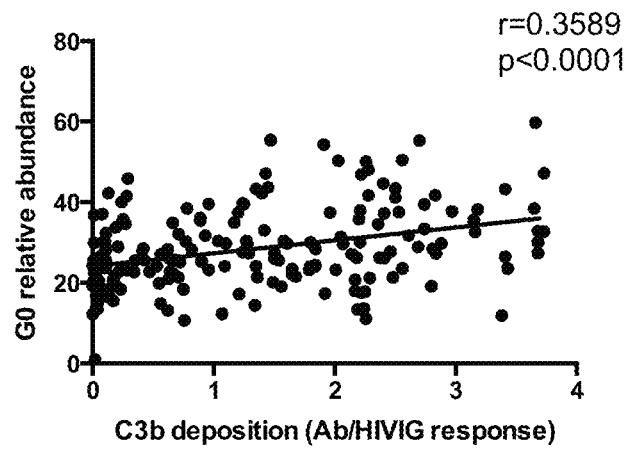
FIG. 9 depicts the antibody glycosylation states associated with transplant rejection.
Figure 9:
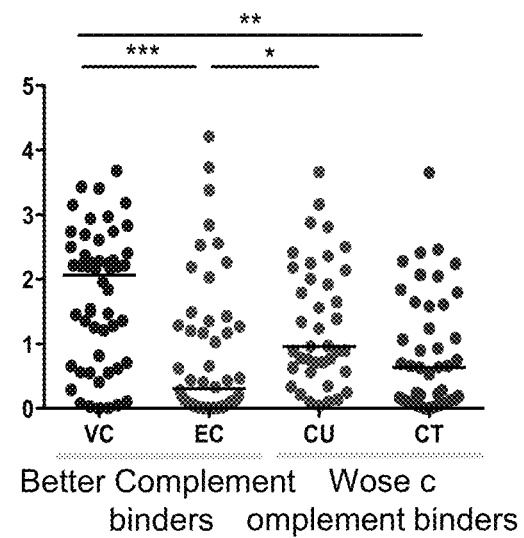
Figure 9:
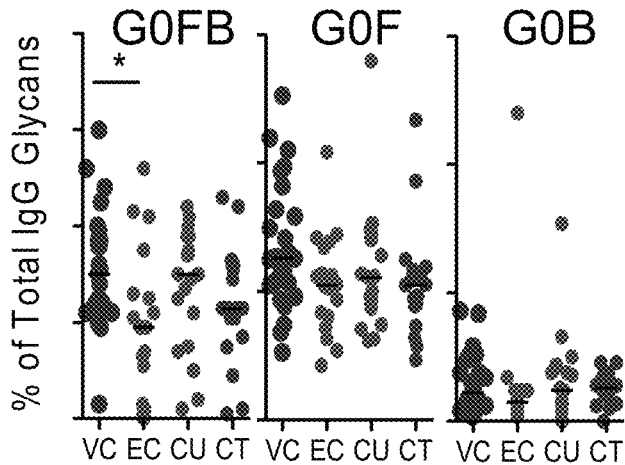

Transplant rejection is associated with elevated anti-HLA antibodies that bind to C1q. C1q antibodies prefer a G0 glycan (A), and specifically, they specifically prefer a G0FB and G0F structure (FIG. 9).

It is specifically contemplated herein that G0FB and G0F antibodies can be targeted as the primary glycoforms that would come up on HLA-specific antibodies as a stronger diagnostic of transplant rejection.

Figure 10:
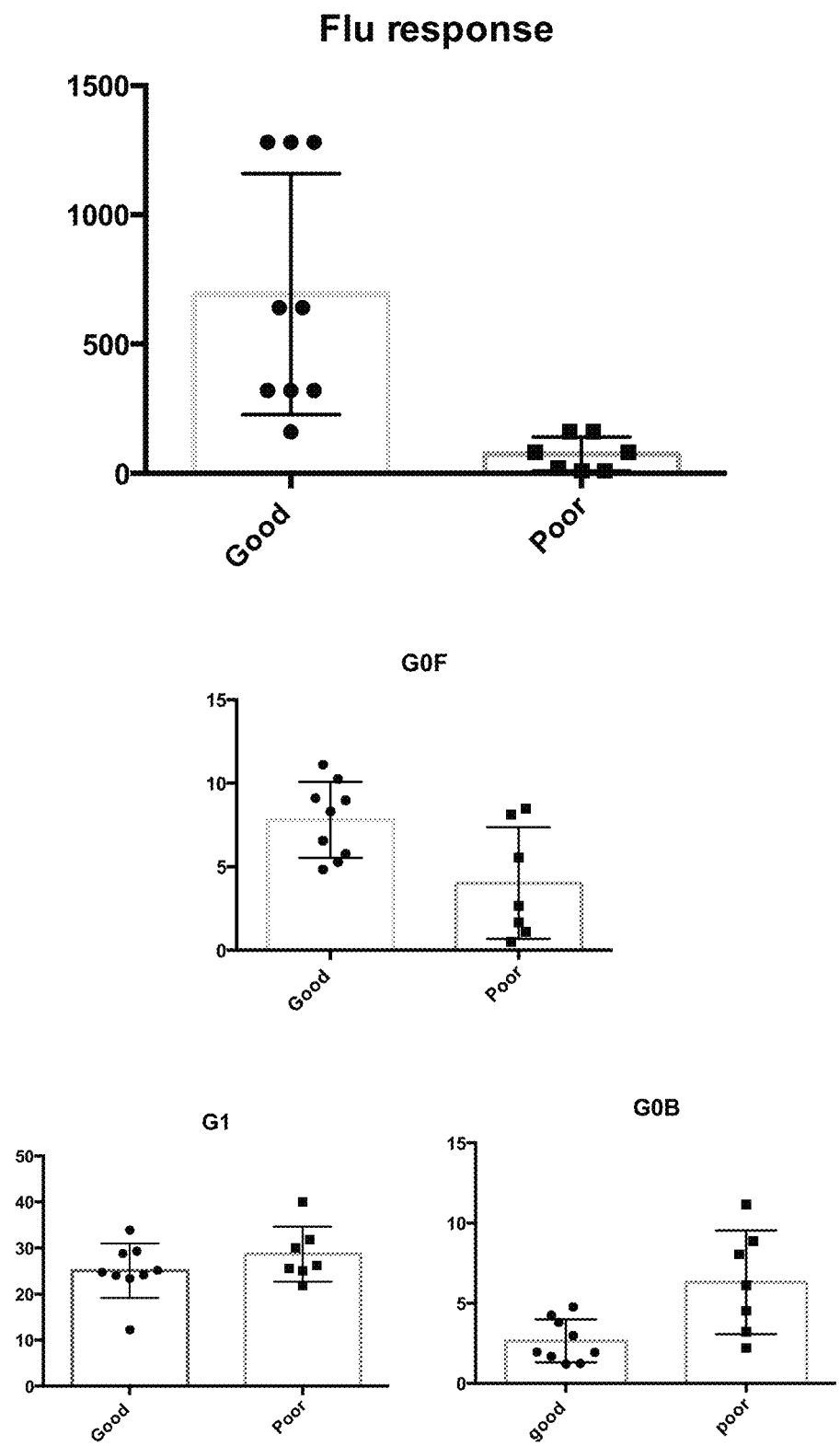
FIG. 10 depicts the antibody glycosylation states associated with flu non-responsiveness.

It is demonstrated herein that flu-non-responsiveness tracks with differential glycosylation of flu-specific antibodies. Good responders make G0F antibodies. Non-responders make G1 and G0B antibodies (FIG. 10). It is contemplated herein that overcoming these effects can help improve flu responsiveness in the elderly. Particularly, the subject can be treated to decrease the amount and/or biological activity of G1 and G0B antibodies in the peripheral blood to improve vaccine responsiveness in the elderly.

LTBI have lower PPD-specific titers than active TB subjects. The importance of TB-specific antibodies in control of TB infection is a highly controversial topic. While TB-specific antibodies are commonly generated upon infection of Mtb, the role of these antibodies remains unclear. To determine if TB specific IgG Ab titers differed between LTBI and active TB subjects, PPD (Purified Protein derivative of TB) ELISA was conducted. Higher levels of PPD-specific IgG were observed in the TBI cohort compared to LTBI subjects (FIG. 1A). This result is most likely due to the higher amount of antigen exposure that occurs in TBI subjects.

Higher PPD-specific ADCC is induced in LTBI. Previous studies have indicated a potential role of innate immune recruiting Ab in the control of several intracellular pathogens including malaria, viral infections and various bacterial infections (28, 29). Thus, to comprehensively compare the innate immune effector profiles of active TB and LTBI individuals, the ability of antibodies to mediate ADCP, ADCC and NK cell degranulation and IFNγ cytokine secretion was tested, normalizing functional activity to PPD-specific titers, due to the significantly higher levels of PPD-specific titers observed in TB subjects (FIG. 1A). No significant difference in ADCP uptake of PPD coated beads into monocytes was observed between the LTBI and TB cohorts (FIGS. 2E-2H). However, in contrast, a modified rapid fluorometric (RF)-ADCC assay that measures the ability of IgG to recruit the cytotoxic capacity of NK cells, showed that LTBI individuals mediate enhanced PPD-specific cytotoxicity as compared to IgG from active TB individuals (p=0.01, FIG. 2F). Furthermore, Abs from both cohorts were also tested for the ability to mediate CD107a degranulation and IFNγ, markers of Ab mediated NK cell cytotoxicity and activation. Similar to ADCC activity, Abs from LTBI subjects were able to induce stronger CD107a degranulation (p=0.0007, FIG. 2G) and IFNγ secretion (FIG. 2H, p=0.007) compared to active TB subjects, thus, indicating that the PPD-specific antibody Fc-effector activity appears to higher in LTBI compared to active TB individuals.

The FcγR binding affinity profile in LTBI patients is more activating and in TB patients more inhibitory. As changes in Fc effector activity are driven by antibody affinity to specific Fc receptors, the hypothesis that the antibodies generated in active TB have a different Fc receptor affinity profile from those generated in LTBI was tested. Surface plasmon resonance (SPR) technology was used to quantify the binding profile of total purified plasma IgGs to activating Fc receptors (FcγRIIa and FcγRIIIa) and inhibitory Fc receptor (FcγRIIb). Interestingly, it was found that the Fc receptor binding to specific Fc receptors differed between LTBI and active TB antibodies. While no differences were observed in binding to FcγRIIa between the two cohorts (p=0.67, FIG. 3A), IgG from LTBI had significantly higher affinity to FcγRIIIa (p<0.0001, FIG. 3C), compared to TB, the key FcγR required for ADCC and NK cell activation.

While both FcγRIIa, and FcγRIIIa are activating receptors involved in mediating Fc-effector functions (30), only engagement of FcγRIIb negatively regulates phagocytes and B cells (31), potentially dampening immune activation, cytokine storm, and plasma cell survival (32). LTBI purified IgG trended towards lower affinity to inhibitory FcγRIIb (p=0.10, FIG. 3B). To estimate the inhibitory role of FcγRIIb upon innate immune effector cell recruitment the ratio of affinity between FcγRIIa:FcγRIIb and FcγRIIIa:FcγRIIb was calculated. LTBI IgG antibodies had significantly increased ratios of both FcγRIIa:FcγRIIb (p=0.03, FIG. 3D) and FcγRIIIa:FcγRIIb binding (p=0.0001, FIG. 3E) compared to TBI IgG. Therefore, preferential binding of LTBI antibodies to activating FcγRIIa and FcγRIIIa which primarily mediate Fc effector functions over inhibitory FcγRIIb engagement potentially account for the higher ADCC, NK cell activity observed on a per antibody basis.

Figure 3H:
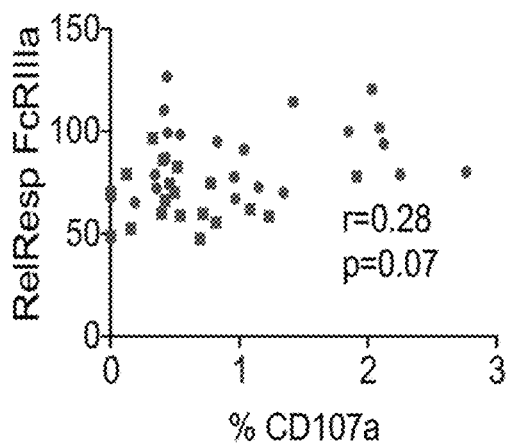
Figure 3I:
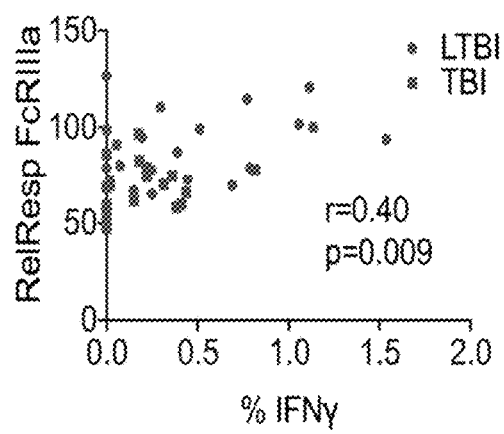
Figure 4A:
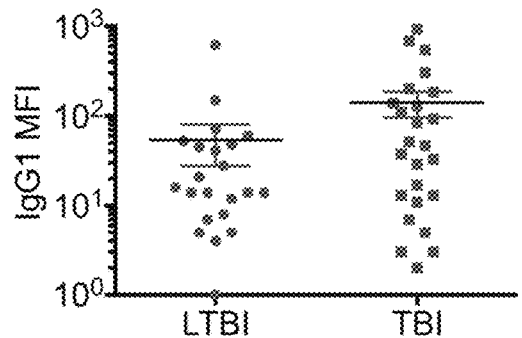
FIGS. 4A-4D demonstrate that IgG3 subclass is higher in TBI subjects. PPD-specific IgG subclass differences were measured by customized luminex assay between LTBI and TBI subjects, comparing PPD-specific (FIG. 4A) IgG1, (FIG. 4B) IgG2, (FIG. 4C) IgG3 and (FIG. 4D) IgG4 isotypes.
Figure 4B:
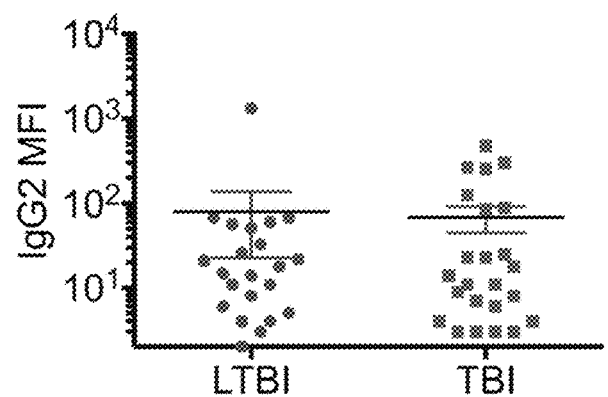
Figure 4C:
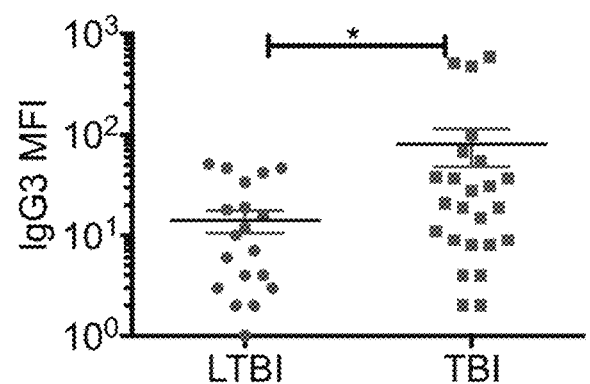
Figure 4D:
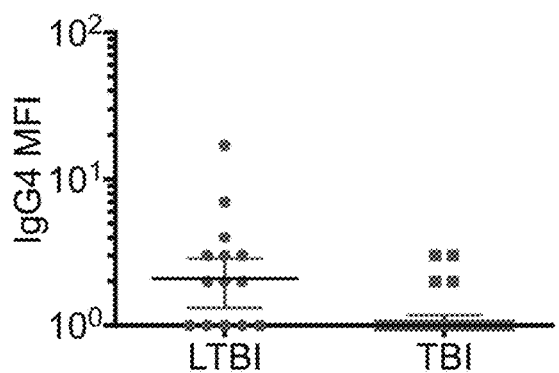

To quantitate the relationship between Fc receptor binding affinity and antibody function, the aforementioned variables were correlated. A significant correlation between ADCC activity and FcγR binding affinity was not detected for either of the TB antibody cohorts (FIG. 3G). In contrast, correlations were observed between ADCP (r=−0.48, p=0.0012), CD107a (r=0.28, p=0.07) and IFNγ (r=0.40, p=0.009) with FcγRIIIa affinities (FIGS. 3G, 3H, and 3I). These data indicate that the differential binding of IgG to FcγRIIIa in particular may be key to the significantly distinct functional abilities in LTBI.

LTBI antibodies mediate killing of intracellular Mtb. The greater ADCC activity of LTBI antibodies indicates that these antibodies can enhance the ability of innate immune cells including NK cells and/or macrophages to control microbial infection. To test this idea directly, the ability of Mtb to survive in human monocyte-derived macrophages (MDM) in the presence of either LTBI, TBI or fetal-cord antibodies with or without NK cells was tested. For this assay, MDM were infected with a virulent strain of Mtb carrying a constitutive and an inducible transcriptional reporter for 24 hours. Relevant IgG purified antibody was then added to the infected cells with or without autologous NK cells and the infection allowed to proceed for an additional 48 hours. The Mtb transcriptional reporter was then induced and cells fixed 24 hours later. Using automated microscopy and custom analysis the total constitutive and inducible Mtb fluorescence signal was quantified within each individual MDM, and the average percentage of transcriptional repression for each condition tested was calculated. A total of three replicates were performed for each antibody. Three independent antibodies were assessed from patients with latent tuberculosis, with an additional three from patients with active disease. The average percentage of transcriptional repression was normalized to PPD titer to objectively compare Ab function.

Figure 11:
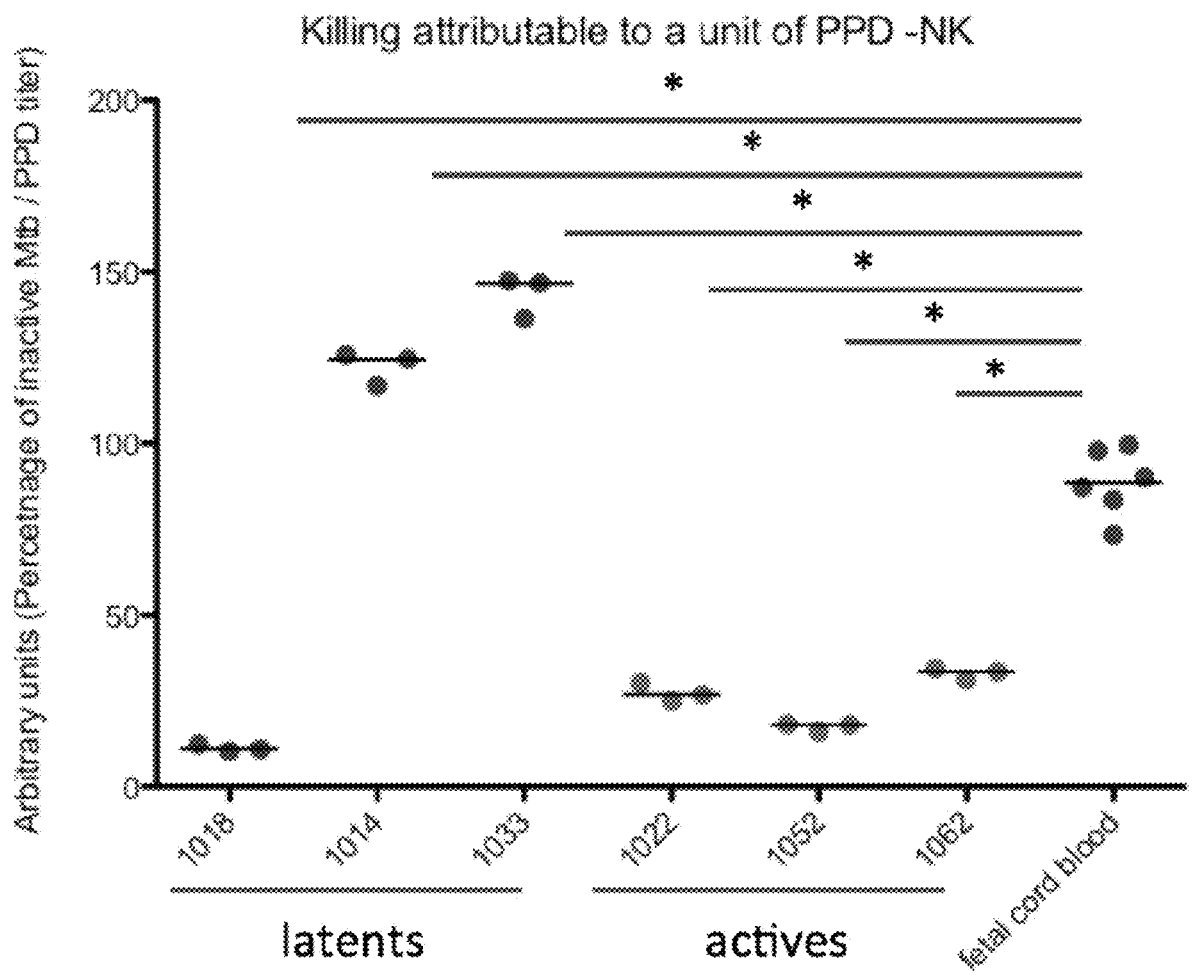
FIG. 11 depicts a graph of the level of the killing attributable to a unit of PPD-NK in latent and active samples.

It was found that the three TBI antibodies samples tested from independent donors were all significantly less able to restrict Mtb transcriptional activity as compared the negative control antibody derived in fetal cord blood (FIG. 11). Conversely, two of the three LTBI antibodies tested significantly enhanced the restriction of Mtb transcriptional activity as compared to either the negative control or TBI antibodies. These effects were independent of the presence of NK cells and were not altered by the presence of NK cells, suggesting that macrophage function was altered by patient antibody. Therefore, antibodies from LBTI are able to significantly reduce the survival of intracellular Mtb as compared to antibodies from TBI patients.

Discussion

It is demonstrated herein that antibodies that recognize Mtb (PPD) in patients with latent TB have an enhanced ability to induce FcR mediated effector mechanisms that can kill Mtb. To our knowledge, this is the first study to examine the innate immune function of antibodies generated during different states of tuberculosis disease and provides a mechanism by which prior studies have shown the protective role of antibodies in TB disease (18, 19). It highlights the importance of FcR glycosylation in establishing not only antibody functionality but also remarks upon the distinct differences between the low inflammatory G2 state in LTBI and high inflammatory G0 state in TBI. Intriguingly, it suggests that ADCC can be decreased with afucosylation. These data together show that when these multiple Fc parameters are combined, there are distinct differences between LTBI and TBI which can be harnessed to develop improved diagnostics to further characterize the continuum of disease between the two states.

While PPD was used here to most broadly and without bias represent the protein spectrum of Mtb, it does also notably contain some lipids and carbohydrates, which arguably constitute a larger portion of Mtb structure. Preliminary data indicates that when broken down into subcellular fractionations, the cytosolic components can be most functionally stimulating from an antibody perspective. (Data not shown.)

Mtb burden is positively correlated with antibody titre. Without wishing to be bound by theory, one model of disease based upon this data may be that in LTBI, there is a decreased inflammatory state. Despite this there is high antibody functionality with ADCC and NK cell activation, which kill Mtb. This may occur heterogeneously at the level of lesions or even individual granulomas containing plasma cells. Ultimately, stochastic events yet to be identified though certainly influenced by immunosuppressive states such as HIV allow for the progression of disease to a much more inflammatory state. Though total IgG antibody titres rise, functionality decreases and it is this loss that may further allow movement along the spectrum to active disease with less Mtb killing and increased bacterial burden.

Indeed, the antibody profiles in LTBI and TBI are distinct in both differ both in biophysical properties and ability to recruit innate immune effector cells. Our understanding of this immune mechanism is expanded herein to determine that less inflammatory afucosylated glycoforms present on of bulk IgG, specifically marked by the reduction of G0 and G0F contribute to increased effector function.

The data presented herein demonstrates that antibodies are capable of controlling intracellular bacteria through NK cell mediated ADCC Despite having lower Mtb (PPD) total IgG titers, LTBI had enhance FcRIIIa mediated Fc-effector functionality compared to TBI. Additionally, the % IgG subclass against Mtb (PPD) were similar between antibodies generated in LTBI and TBI. These data indicate that unlike other intracelluar pathogens, such as HIV, specific IgG subclasses may not be the critical determinate of an effective humoral response. Instead, the present results indicate that generating Mtb-specific antibodies of specific glycan structures is of greater importance. However, testing for Mtb-specific binding through PPD binding alone may not be an accurate enough antigen to represent Mtb infection. Previous studies have identified specific antigens commonly recognized by TBI subjects (38), in addition passive immunization of mAb studies in animals, recognizing specific mTB antigens has been shown to be protective (13, 14).

In addition to the need for an effective vaccine against pulmonary tuberculosis, a rapid point-of-care diagnostic with the ability to discern active tuberculosis from latent is of critical important. The differential Fc receptor binding profiles of antibodies generated during LTBI and TBI provides a novel and compelling biomarker for such diagnostic capabilities.

Surprisingly, IgG with enhanced ADCC ability was found in subjects with latent disease states. Altogether, this data indicates that this ADCC can be harnessed to control Mtb.

REFERENCES

1. Anonymous (2010) Global Tuberculosis Control . . . World Health Organization.
2. Whalen C C (2005) Diagnosis of latent tuberculosis infection: measure for measure. *JAMA: the journal of the American Medical Association* 293(22): 2785-2787.
3. Fine P E (1988) BCG vaccination against tuberculosis and leprosy. *British medical bulletin* 44(3): 691-703.
4. Newton S M, Brent A J, Anderson S, Whittaker E, & Kampmann B (2008) Paediatric tuberculosis. *The Lancet infectious diseases* 8(8):498-510.
5. Kunnath-Velayudhan S, et al. (2010) Dynamic antibody responses to the *Mycobacterium tuberculosis* proteome. *Proceedings of the National Academy of Sciences of the United States of America* 107(33):14703-14708.
6. Ellner J J, Hirsch C S, & Whalen C C (2000) Correlates of protective immunity to *Mycobacterium tuberculosis* in humans. *Clinical infectious diseases: an official publication of the Infectious Diseases Society of America* 30 Suppl 3:S279-282.
7. Lin P L, et al. (2014) Sterilization of granulomas is common in active and latent tuberculosis despite within-host variability in bacterial killing. *Nat Med* 20(1):75-79.
8. Achkar J M & Casadevall A (2013) Antibody-mediated immunity against tuberculosis: implications for vaccine development. *Cell host & microbe* 13(3):250-262.
9. Kozakiewicz L, Phuah J, Flynn J, & Chan J (2013) The role of B cells and humoral immunity in *Mycobacterium tuberculosis* infection. *Advances in experimental medicine and biology* 783:225-250.
10. Costello A M, et al. (1992) Does antibody to mycobacterial antigens, including lipoarabinomannan, limit dissemination in childhood tuberculosis? *Transactions of the Royal Society of Tropical Medicine and Hygiene* 86(6): 686-692.
11. Pethe K, et al. (2001) The heparin-binding haemagluttinin of *M. tuberculosis* is required for extrapulmonary dissemination. *Nature* 412(6843): 190-194.
12. de Valliere S, Abate G, Blazevic A, Heuertz R M, & Hoft D F (2005) Enhancement of innate and cell-mediated immunity by antimycobacterial antibodies. *Infection and immunity* 73(10):6711-6720.
13. Abebe F & Bjune G (2009) The protective role of antibody responses during *Mycobacterium tuberculosis* infection. *Clinical and experimental immunology* 157(2): 235-243.
14. Teitelbaum R, et al. (1998) A mAb recognizing a surface antigen of *Mycobacterium tuberculosis* enhances host survival. *Proceedings of the National Academy of Sciences of the United States of America* 95(26):15688-15693.
15. Maglione P J, Xu J, Casadevall A, & Chan J (2008) Fc gamma receptors regulate immune activation and susceptibility during *Mycobacterium tuberculosis* infection. *Journal of immunology* 180(5):3329-3338.
16. Huber M & Trkola A (2007) Humoral immunity to HIV-1: neutralization and beyond. *J Intern Med* 262(1): 5-25.
17. Nabavi N & Murphy J W (1986) Antibody-dependent natural killer cell-mediated growth inhibition of Cryptococcus neoformans. *Infection and immunity* 51(2):556-562.
18. Goh Y S, et al. (2011) Human IgG isotypes and activating Fcgamma receptors in the interaction of *Salmonella enterica* serovar Typhimurium with phagocytic cells. *Immunology* 133(1):74-83.
19. Modolell M, Schaible U E, Rittig M, & Simon M M (1994) Killing of Borrelia burgdorferi by macrophages is dependent on oxygen radicals and nitric oxide and can be enhanced by antibodies to outer surface proteins of the spirochete. *Immunology letters* 40(2):139-146.
20. Brerski R J, et al. (2009) Tumor-associated and microbial proteases compromise host IgG effector functions by a single cleavage proximal to the hinge. *Proceedings of the National Academy of Sciences of the United States of America* 106(42): 17864-17869.
21. Vincents B, von Pawel-Rammingen U, Bjorck L, & Abrahamson M (2004) Enzymatic characterization of the streptococcal endopeptidase, IdeS, reveals that it is a cysteine protease with strict specificity for IgG cleavage due to exosite binding. *Biochemistry* 43(49):15540-15549.
22. Ackerman M E, et al. (2011) A robust, high-throughput assay to determine the phagocytic activity of clinical antibody samples. *J lmmunol Methods* 366(1-2):8-19.
23. Darrah P A, et al. (2007) Multifunctional TH1 cells define a correlate of vaccine-mediated protection against Leishmania major. *Nature medicine* 13(7):843-850.
24. Gomez-Roman V R, et al. (2006) A simplified method for the rapid fluorometric assessment of antibody-dependent cell-mediated cytotoxicity. *J lmmunol Methods* 308 (1-2):53-67.
25. Chung A W, Rollman E, Center R J, Kent S J, & Stratov I (2009) Rapid degranulation of NK cells following activation by HIV-specific antibodies. *J lmmunol* 182(2): 1202-1210.
26. Brown E P, et al. (2012) High-throughput, multiplexed IgG subclassing of antigen-specific antibodies from clinical samples. *Journal of immunological methods* 386(1-2):117-123.
27. Murphy K P (2012) *Machine learning: a probabilistic perspective* (MIT Press, Cambridge, Mass.) pp xxix, 1067 p.
28. Richards J S, et al. (2010) Association between naturally acquired antibodies to erythrocyte-binding antigens of Plasmodium falciparum and protection from malaria and high-density parasitemia. *Clinical infectious diseases: an official publication of the Infectious Diseases Society of America* 51(8):e50-60.
29. Ackerman M E, Dugast A S, & Alter G (2012) Emerging concepts on the role of innate immunity in the prevention and control of HIV infection. *Annual review of medicine* 63:113-130.
30. Nimmerjahn F & Ravetch J V (2008) Analyzing antibody-Fc-receptor interactions. *Methods Mol Biol* 415: 151-162.
31. Baerenwaldt A, et al. (2011) Fcgamma receptor IIB (FcgammaRIIB) maintains humoral tolerance in the human immune system in vivo. *Proceedings of the National Academy of Sciences of the United States of America* 108(46):18772-18777.
32. Smith K G & Clatworthy M R (2010) FcgammaRIIB in autoimmunity and infection: evolutionary and therapeutic implications. *Nature reviews. Immunology* 10(5):328-343.
33. Arnold J N, Wormald M R, Sim R B, Rudd P M, & Dwek R A (2007) The impact of glycosylation on the biological function and structure of human immunoglobulins. *Annual review of immunology* 25:21-50.

34. Raju T S (2008) Terminal sugars of Fc glycans influence antibody effector functions of IgGs. *Curr Opin Immunol* 20(4):471-478.
35. Ferrara C, et al. (2011) Unique carbohydrate-carbohydrate interactions are required for high affinity binding between FcgammaRIII and antibodies lacking core fucose. *Proceedings of the National Academy of Sciences of the United States of America* 108(31):12669-12674.
36. Niwa R, et al. (2005) IgG subclass-independent improvement of antibody-dependent cellular cytotoxicity by fucose removal from Asn297-linked oligosaccharides. *J Immunol Methods* 306(1-2):151-160.
37. Zou G, et al. (2011) Chemoenzymatic synthesis and Fcgamma receptor binding of homogeneous glycoforms of antibody Fc domain. Presence of a bisecting sugar moiety enhances the affinity of Fc to FcgammaIIIa receptor. *Journal of the American Chemical Society* 133(46): 18975-18991.
38. Wu X, et al. (2010) Comparison of antibody responses to seventeen antigens from *Mycobacterium tuberculosis*. *Clinica chimica acta; international journal of clinical chemistry* 411(19-20):1520-1528.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A method of treating active tuberculosis in a subject, the method comprising:
    assaying a sample obtained from the subject to determine, for an antibody, the presence or absence of an antibody glycosylation state indicative of active tuberculosis; and
    administering a treatment for tuberculosis if the antibody glycosylation state is indicative of the presence of active tuberculosis;
    wherein the antibody is an IgG antibody that is antigen specific to tuberculosis and wherein the glycosylation state indicative of active tuberculosis is selected from the group consisting of:
    decreased 2-galactose (G2); decreased fucosylated G2 (G2F); decreased fucosylated G2 with bisecting N-acetylglucosamine (G2FB); and decreased 2-galactose (G2), fucosylated G2 (G2F), and fucosylated G2 with bisecting N-acetylglucosamine (G2FB).

2. The method of claim 1, wherein the antibody is from the plasma of the subject.

3. The method of claim 1, wherein the treatment comprises a therapeutically effective dosage of antibody with a normal level of glycosylation relative to a healthy individual.

* * * * *